(12) United States Patent
Federoff et al.

(10) Patent No.: US 8,119,118 B2
(45) Date of Patent: Feb. 21, 2012

(54) HELPER VIRUS-FREE HERPESVIRUS AMPLICON PARTICLES AND USES THEREOF

(75) Inventors: Howard J. Federoff, Rochester, NY (US); William J. Bowers, Webster, NY (US); John G. Frelinger, Pittsford, NY (US); Richard A. Willis, Denver, CO (US); Thomas G. Evans, Davis, CA (US); Stephen Dewhurst, Rochester, NY (US); Khaled A. Tolba, Rochester, NY (US); Joseph D. Rosenblatt, Ft. Lauderdale, FL (US)

(73) Assignee: University of Rochester, Rochester, NY (US)

(*) Notice: Subject to any disclaimer, the term of this patent is extended or adjusted under 35 U.S.C. 154(b) by 635 days.

(21) Appl. No.: 11/244,726

(22) Filed: Oct. 5, 2005

(65) Prior Publication Data
US 2006/0204477 A1    Sep. 14, 2006

Related U.S. Application Data

(63) Continuation of application No. 09/997,848, filed on Nov. 29, 2001, now abandoned.

(60) Provisional application No. 60/250,079, filed on Nov. 30, 2000, provisional application No. 60/253,858, filed on Nov. 29, 2000.

(51) Int. Cl.
*A01N 63/00* (2006.01)
*A61K 48/00* (2006.01)
*G09B 5/04* (2006.01)

(52) U.S. Cl. .................... 424/93.2; 435/320.1

(58) Field of Classification Search ........................ None
See application file for complete search history.

(56) References Cited

U.S. PATENT DOCUMENTS

| | | | |
|---|---|---|---|
| 5,501,979 A | 3/1996 | Geller et al. | 435/320.1 |
| 5,661,033 A | 8/1997 | Ho et al. | |
| 5,763,217 A | 6/1998 | Cynader et al. | |
| 5,851,826 A | 12/1998 | Fraefel et al. | 435/325 |
| 5,928,913 A | 7/1999 | Efstathiou et al. | 435/172.3 |
| 5,965,441 A | 10/1999 | Breakefield et al. | 435/456 |
| 5,998,208 A | 12/1999 | Fraefel et al. | 435/455 |
| 6,040,172 A | 3/2000 | Kaplitt | |
| 6,051,428 A | 4/2000 | Fong et al. | 435/456 |
| 6,344,445 B1 | 2/2002 | Boursnell et al. | |
| 6,635,478 B1 | 10/2003 | Hippenmeyer et al. | |
| 2002/0103152 A1 | 8/2002 | Kay et al. | |
| 2004/0047837 A1 | 3/2004 | Fong et al. | |

FOREIGN PATENT DOCUMENTS

| | | |
|---|---|---|
| CN | 1263159 | 8/2000 |
| WO | WO 96/29421 | 9/1996 |
| WO | WO 97/00085 | 1/1997 |
| WO | WO 98/15637 | 4/1998 |
| WO | WO 99/27944 | 6/1999 |
| WO | WO 00/08194 | 2/2000 |
| WO | WO 00/34497 | 6/2000 |
| WO | WO 01/89304 | 11/2001 |
| WO | WO02/053576 | 7/2002 |
| WO | WO 02/056828 | 7/2002 |
| WO | WO 02/087625 | 11/2002 |

OTHER PUBLICATIONS

Oyama et al., 1998, The Journal of Immunology, 160: 1224-1232.*
Chen and Wu, 1998, J. Biomed Sci., 5: 231-252.*
Platt, 1998, Nature, 392 supplement: 11-17.*
Bowers et al., 2001, Gene Therapy, 8: 111-120.*
Herrlinger et al., 2000, Human Gene Therapy, 11: 1429-1438.*
Morse et al., 1998, Cancer Research 58: 2965-2968.*
Gilboa et al., 1998, Cancer Immunol. Immunother., 46: 82-87.*
Whitley et al., 1998, Clinical Infectious Diseases 26: 541-553.*
Read et al., 1993, Journal of Virology, 67: 7149-7160.*
Bowers et al., "Expression of vhs and VP16 during HSV-1 helper virus-free amplicon packaging enhances titers, " Society for Neuroscience Abstracts, vol. 26, No. 1-2, pp. Abstract No.-765.10, XP009062401, 30th Annual Meeting of the Society of Neuroscience; New Orleans, LA, USA, Nov. 4-9, 2000.
Bowers et al., "Neurotrophin-3 transduction attenuates cisplatin spiral ganglion neuron ototoxicity in the cochlea," Molecular Therapy, vol. 6, No. 1, pp. 12-18, Jul. 2002.
Fink et al., "Engineering herpes simplex virus vectors for gene transfer to neurons," Nature Medicine, vol. 3, No. 3, pp. 357-359, 1997.
Gorantla et al., "Human dendritic cells transduced with herpex simplex virus amplicons encoding human immunodeficiency virus type 1 (HIV-1) gp120 elicit adaptive immune responses from human cells engrafted into NOD/SCID mice and confer partial protection against HIV-1 challenge," J. Virol., vol. 79, No. 4, pp. 2124-2132, Feb. 2005.
Hocknell et al., "Expression of human immunodeficiency virus type 1 gp120 from herpes simplex virus type 1-derived amplicons results in potent specific, and durable cellular and humoral immune responses," J. Virol., vol. 76, No. 11, pp. 5565-5580, Jun. 2002.
Olschowka et al., "Helper-free HSV-1 amplicons elicit a markedly less robust innate immune response in the CNS," Molecular Therapy; vol. 7, No. 2, pp. 218-227, Feb. 2003.
Saeki et al., "Improved helper virus-free packaging system for HSV amplicon vectors using an ICP27-deleted, oversized HSV-1 DNA in a bacterial artificial chromosome," Molecular Therapy, vol. 3, No. 4, pp. 591-601, Apr. 2001.

(Continued)

*Primary Examiner* — Joanne Hama
(74) *Attorney, Agent, or Firm* — McKeon, Meunier, Carlin & Curfman, LLC

(57) ABSTRACT

The invention features new helper virus-free methods for making herpesvirus amplicon particles that can be used in immunotherapies, including those for treating any number of infectious diseases and cancers (including chronic lymphocytic leukemia, other cancers in which blood cells become malignant, lymphomas (e.g. Hodgkin's lymphoma or non-Hodgkin's type lymphomas). Described herein are methods of making helper virus-free HSV amplicon particles; cells that contain those particles (e.g., packaging cell lines or patients' cells, infected in vivo or ex vivo); particles produced according to those methods; and methods of treating a patient with an hf-HSV particle made according to those methods.

48 Claims, 13 Drawing Sheets

OTHER PUBLICATIONS

Tolba et al., "Herpes simplex virus (HSV) amplicon-mediated codelivery of secondary lymphoid tissue chemokine and CD40L results in augmented antitumor activity," Cancer Research, vol. 62; No. 22, pp. 6545-6551, Nov. 15, 2002.

Wang et al., "HSV-1 amplicon-vectors are a highly efficient gene delivery system for skeletal muscle myoblasts and myotubules," Am. J. Physiol., 278(3):C619-26, Mar. 2000.

Wang et al., "Cellular immune responses to helper-free HSV-1 amplicon particles encoding HSV-1 gp120 are enhanced by DNA priming," Vaccine, vol. 21, No. 19-20, pp. 2288-2297, Jun. 2, 2003.

Arvanian V.L. et al., "Removal of NMDA Receptor Mg+2 Block Extends the Action of NT-3 on Synaptic Transmission in Neonatal Rat Motoneurons", J. Neurophysiol. Jul. 2001, vol. 86, No. 1, pp. 123-129.

Bowers W.J. et al., "Discordance Between Expression and Genome Transfer Titering of HSV Amplicon Vectors: Recommendation for Standardized Enumeration", Molecular Therapy, Mar. 2000, vol. 1, No. 3, pp. 294-299.

Chow, Yen-Huang et al., "Improvement of Hepatitis B Virus DNA Vaccines by Plasmids Coexpressing Hepatitis B Surface Antigen and Interleukin-2", Journal of Virology, vol. 71, No. 1, pp. 169-178, Jan. 1997.

Croce et al., "The Use of Carbohydrate Antigens for the Preparation of Vaccines for Therapy in Breast Cancer", Drugs of Today, 2002, vol. 38, No. 11 pp. 759-768.

De Felipe P. et al., "Integrating Retoviral Cassette Extends Gene Delivery of HSV-1 Expression Vectors to Dividing Cells", Biotechniques, Aug. 2001, vol. 31, No. 2, pp. 394-402.

El-Farrash et al., "Generation and Characterization of a Human Immunodeficiency Virus Type 1 (HIV-1) Mutant Resistant to an HIV-1 Protease Inhibitor", Journal of Virology, 68:233-239 (1994).

Haase G. et al., "Gene Therapy of Murine Motor Neuron Disease Using Adenoviral Vectors for Neurotrophic Factors", Nat. Med., Apr. 1997, vol. 3, No. 4, pp. 429-436.

Harris et al., "Keyhole Limpet Hemocyanin: Molecular Structure of a Potent Marine Immunoactivator", Euro. Urol. 2000, vol. 37 (Suppl. 3), pp. 24-33.

Karpoff, Howard M. et al., "Prevention of Hepatic Tumor Metastases in Rats With Herpes Viral Vaccines and γ-Interferon", J. Clin. Invest., vol. 99, No. 4, pp. 799-804, Feb. 1997.

Maguir-Zeis Ka et al., "HSV Vector-Mediated Gene Delivery to the Central Nervous System", Current Opinion Molecular Therapy, Oct. 2001, vol. 3, No. 5, pp. 482-490.

Marsh D.R. et al., "Herpes Simplex Viral and Amplicon Vector-Mediated Gene Transfer Into Glia and Neurons in Organotypic Spinal Cord and Dorsal Root Ganglion Cultures", Molec. Therap. May 2000, vol. 1. No. 5, pp. 464-478.

Sena-Estaves et al., "HSV-1 Amplicon Vectors—Simplicity and Versatility", Molecular Therapy, Jul. 2000, vol. 2, No. 1, pp. 9-15.

Sun M. et al., "Improved Titers for Helper Virus-Free Herpes Simplex Virus Type 1 Plasmid Vectors by Optimization of the Packaging Protocol and Addition of Noninfectious Herpes Simplex Virus-Related Particles (Previral DNA Replication Enveloped Particles) to the Packaging Procedure", Human Gene Therapy, Aug. 10, 1999, vol. 10, pp. 2005-2011.

Yu et al., "High Efficiency In Vitro Gene Transfer Into Vascular Tissues Using a Pseudotyped Retroviral Vector Without Pseudotransduction", *Gene Therapy*, 6:1876-1883 (1999).

Alexander et al. "Transfer of Contaminants in Adeno-Associated Virus Vector Stocks Can Mimic Transduction and Lead to Artifactual Results", Human Gene Therapy, pp. 8:119-1920 (Nov. 1, 1997).

Andreeff et al., "Discrimination of Human Leukemia Subtypes by Flow Cytometric Analysis of Cellular DNA and RNA", Blood, vol. 55, No. 2, pp. 282-293, (Feb. 1980).

Bogen et al., "Idiotope-Specific T Cell Clones That Recognize Syngeneic Immunoglobulin Fragments in the Context of Class II Molecules", Eur. J. Immunol., vol. 16, pp. 1373-1378, (1986).

Bogen et al., "Processing and Presentation of Idiotypes to MHC-Restricted T Cells", Intern. Rev. Immunol., vol. 10, pp. 337-355 (1993).

Cantwell, et al., "Adenovirus Vector Infection of Chronic Lymphocytic Leukemia B Cells", Blood, vol. 88, No. 12, pp. 4676-4683, (Dec. 15, 1996).

Caligaris-Cappio et al., "B-Cell Chronic Lymphocytic Leukemia: A Bird of a Different Feather", Journ. Of Clinical Oncology, vol. 17, No. 1, pp. 399-408, (Jan. 1999).

Cardoso et al., "Pre-B Acute Lymphoblastic Leukemia Cells May Induce T-Cell Anergy to Alloantigen", Blood, vol. 88, No. 1, pp. 41-48, (Jul. 1, 1996).

Collins, M., "Retroviral Vectors for Cancer Gene Therapy", Springer-Verlag Berlin Heidelberg New York, ISSN 0947-6075 an ISBN 3-540-67298-2, pp. 100-105, 2000.

Cunningham et al., "A Cosmid-Based System for Constructing Mutants of Herpes Simplex Virus Type 1", Virology 197, pp. 116-124 (1993).

Diehl et al., "CD40 Activation in vivo Overcomes Peptide-Induced Peripheral Cytotoxic T-Lymphocyte Tolerance and Augments Anti-Tumor Vaccine Efficacy", Nature Medicine, vol. 5, No. 7, pp. 774-779 (Jul. 1999).

Döhner et al., "Chromopsome Aberrations in B-Cell Chronic Lymphocytic Leukemia: Reassessment Based on Molecular Cytogenetic Analysis", J. Mol. Med., 77:266-281 (1999).

Everly, Jr., et al., "Mutational Analysis of the Virion Host shutoff Gene (LUL41) of Herpes Simplex Virus (HSV): Characterization of HSV Type 1 (HSV-1) HSV-2 Chimeras", Journal of Virology, vol. 71, No. 10, pp. 7157-7166, (Oct. 1997).

Everly, Jr., et al., "Site-Directed Mutagenesis of the Virion Host Shutoff Gene (UL41) of Herpes Simplex Virus (HSV): Analysis of Functional Differences between HSV Type 1 (HSV-1) and HSV-2 Alleles", Journal of Virology, vol. 73, No. 11, pp. 9117-9129, (Nov. 1999).

Fraefel et al., "Helper Virus-Free Transfer of Herpes Simplex Virus Type 1 Plasmid Vectors into Neural Cells", Jouranl of Virology, vol. 70, No. 10, pp. 7190-7197 (Oct. 1996).

Frenkel et al., "Minereview: The Herpes Simplex Virus Amplicon—A Versatile Defective Virus Vector", Gene Therapy, vol. 1, Suppl. 1, pp. S40-S46, (1994).

Frenkel et al., "The Herpes Simplex Virus Amplicon—A Novel Animal Virus Cloning Vector", Eukaryotic Viral Vectors, pp. 205-209, by Cold spring harbor Laboratory (1982).

Geller et al., "Helper Virus-Free Herpes Simplex Virus-1 Plasmid Vectors for Gene Therapy of Parkinson's Disease and Other Neurological Disorders"; *Experimental Neurology*, vol. 144, No. 1, pp. 98-102 (1997).

Geller, "A New Method to Propagate Defective HSV-1 Vectors", Nucleic Acids Research, vol. 16, No. 12, pp. 5690, (1988).

Geller et al., "A Defective HSV-1 Vector Expresses, *Escherichia coli*&Galactosidase in Cultured Peripheral Neurons", Science, vol. 241, pp. 1667-1169, (Sep. 23, 1988).

Geller et al., "An Efficient Deletion Mutant Packaging System for Defective Herpes Simplex Virus Vectors: Potential Applications to Human Gene Therapy and Neuronal Physiology", Proc. Natl. Acad. Sci., USA, vol. 87, No. 22, pp. 8950-8954, (Nov. 1990).

Geschwind et al., "Transfer of the Never Growth Factor Gene into Cell Lines and Cultured Neurons Using a Defective Herpes Simplex Virus Vector. Transfer of the NGF Gene into Cells by a HSV-1 Vector", Molecular Brain Research, vol. 24, pp. 327-335,(1994).

Grewal et al., "The Role of CD40 Ligand in Costimulation and T-Cell Activation", Immunological Reviews, No. 153, pp. 86-105, (1996).

Gruss et al., "CD40/CD40 Ligand Interactions in Normal, Reactive and Malignant Lympho-Hematopoietic Tissues", Leukemia and Lymphoma, vol. 24, No. 5/6, pp. 393-422 (1997).

Hardwicke et al., "Differential Effects of Nerve Growth Factor and Dexamethasone on Herpes Simplex Virus Type 1 oriL- and OriS-Dependent DNA Replication in PC12 Cells", Journ. Of Virology, vol. 71, No. 5, pp. 3580-357, (May 1997).

Hirano, et al., "Expression of Costimulatory Molecules in Human Leukemias", Leukemia, vol. 10, No. 7, pp. 1168-1176, (Mar. 21, 1996).

Hitt et al., "Human Adenovirus Vectors for Gene Transfer into Mammalian Cells", Gene Therapy, Advances in Pharmacology, vol. 40, pp. 137-206, (1997).

Howard et al., "Genetic Manipulation of Primitive Leukemic and Normal Hematopoietic Cells Using a Novel Method of Adenovirus-Mediated Gene Transfer", Leukemia, vol. 13, No. 10, pp. 1608-1616, (Oct. 1999).

Huang et al., "Efficient Adenovirus-Mediated Gene Transduction of Normal and Leukemic Hematopoietic Cells", Gene Therapy, vol. 4, No. 10, pp. 1093-1099 (Oct. 1997).

Karr et al., "The *Virion Host Shutoff* Function of Herpes Simplex Virus Degrades the 5' End of a Target mRNA before the 3' End", Virology, vol. 264, No. 1, pp. 195-204, (1999).

Khanna et al., "Cutting Edge: Engagement of CD40 Antigen with Soluble CD40 Ligand Up-Regulates Peptide Transporter Expression and Restores Endogenous Processing Function in Burkitt's Lymphoma Cells", The Journ. of Immunology, vol. 159, No. 12, pp. 5783-5785 (Dec. 15, 1997).

Kochanek, "High-Capacity Adenoviral Vectors for Gene Transfer and Somatic Gene Therapy", Human Gene Therapy, vol. 10, No. 15, pp. 2451-2459, (Oct. 10, 1999).

Kutubuddin et al., "Eradication of pre-established Lymphoma Using Herpes Simplex Virus Amplicon Vectors", Bloo, vol. 93, No. 2 pp. 643-654, (Jan. 15, 1999).

Kwak et al., "Induction of Immune Responses in Patients with B-Cell Lymphoma Against the Surface-Immunoglobulin Idiotype Expressed by Their Tumors", The New England Journal of Medicine, vol. 327, No. 17, pp. 1209-1215, (Oct. 22, 1992).

Kwong et al., "The Herpes Simplex Virus Virion Host Shutoff Function", vol. 63, No. 11, pp. 4834-4839, (Nov. 1989).

Lam et al., "Herpes Simplex Virus VP16 Rescues Viral mRNA from Destruction b the Virion Host Shutoff Function", The EMBO Journal, vol. 15, No. 10, pp. 2575-2581, (May 15, 1996).

Lanzavecchia, "Licence to Kill", Nature, vol. 393, pp. 413-414, (Jun. 4, 1998).

Lieb et al., "Gene Delivery to Neurons: Is Herpes Simplex Virus the Right tTool for the Job?", BioEssays, vol. 15, No. 8 pp. 547-554, (Aug. 1993).

Lillycrop et al., "The Octamer-Binding Protein Oct-2 Represses HSV Immediate-Early Genes in Cell Lines Derived from Latently Infectble Sensory Neurons", Neuron, vol. 7, No. 3, pp. 381-390,(Sep. 1991).

Liu et al., "Pseudotransduction of Hepatocytes by Using Concentrated Pseudotyped Vesicular Stomatitis Virus G Glycoprotein (VSV-G)-Maloney Murine Leukemia Virsu-Derived Retrovirus Vectors: Comparison of VSV-G and Amphotropic Vectors for Hepatic Gene Transfer", Journal of Virology, vol. 70, No. 4, pp. 2497-2502, (Apr. 1996).

Lu et al., "Herpes Simplex Virus Type 1 Amplicon Vectors with Glucocorticoid-Inducible Gene Expression", Human Gene Theraphy, vol. 6, No. 4, pp. 419-428, (Apr. 1995).

Mader et al., "A Steroid-Inducible Promotr for the Controlled Overexpression of Cloned Genes in Eukaryotic Cells", Proc. Natl. Acad. Sci. USA, vol. 90. pp. 5603-5607, (Jun. 1993).

Martuza et al, "Experimental Therapy of Human Glioma by Means fo a Geneticlaly Engineered Virus Mutant", Science, vol. 252, pp. 854-856 (May 10, 1991).

Matzinger, "The JAM Test a Simple assay for DNA Fragmentation and Cell Death", Journ. of Immunological Methods, vol. 145, pp. 185-192 (1991).

McFarlane et al., "Hexamethylene Bisacetamide Stimulates Herpes Simplex Virus Immediate early Gene Expression in the Absence of Trans-Induction by Vmw65", Journal of General Virology, vol. 73, pp. 285-292, (1992).

Mellerick et al., "Physical State of the Latent Herpes Simplex Virus Genome in a Mouse Model System: Evidence Suggesting and Episomal State", Virology, vol. 158, pp. 265-275, (1987).

O'Hare et al., "Herpes Simplex Virus Regulatory Elements and the Immunoglobulin Octamer Domain Bind a Common kfactor and are both Targets for Virion Transactivation", Cell, vol. 52, pp. 435-445, (Feb. 12, 1988).

O'Hare, "The Virion Transactivator of Herpes Simplex Virus", Virology, vol. 4, pp. 145-155, (1993).

Palella et al., "Herpes Simplex Virsu-Mediated Human Hypoxanthine-Guanine Phosphoribosyltransferase Gene Transfer into Neuronal Cells", Molecular and Cellular Biology, vol. 8 No. 1, pp. 457-460 (Jan. 1988).

Paterson et al., "A Prominent Serine-Rich Region in Vmw175, the Major Transcriptional Regulator protein of Herpes Simplex Virus Type 1, is not Essential for Virus Growth in Tissue Culture", Journal of General Virology, vol. 71, pp. 1775-1783 (1990).

Post et al., "Regulation of a a Genes of Herpes Simplex Virus: Expression of Chimeric Genes Produced by Fusion of Thymidine Kinase with a α Gene Promoters", Cell, vol. 24, pp. 555-565, (May 1981).

Preston, et al., "A Complex Formed between Cell Components and an HSV Structural Polypeptide Binds to a Viral Immediate Early Gene Regulatory DNA Sequence", Cell, vol. 52, pp. 425-434, (Feb. 12, 1988).

Read et al., "Herpes Simplex Virus Mutants Defective in the Virion-Associated Shutoff of Host Polypeptide Synthesis and Exhibiting Abnormal Synthesis of α (Immedate Early) Viral Polypeptides", Journal of Virology, vol. 46, No. 2, pp. 498-512 (May 1983).

Rixon et al., "Assembly of Enveloped Tegument Structures (L particles) Can Occur Independently of Virion Maturaiton in Herpes Simplex Virus Tye 1-Infected Cells", Journal of General Viology, vol. 73, pp. 277-284 (1992).

Roizman, "HSV Gene Functions: What Have we Learned that could be Generally Applicable to its Near and Distant Cousins?", Acta Virologia, vol. 43, pp. 75-80, (1999).

Saekl et al., "Herpes Simplex Virus Type 1 DNA Amplified as Bacterial Artificial Chromosome in *Escherichia coli*: Rescue of Replication-Competent Virus Progeny and Packaging of Amplicon Vectors", Human Gene Therapy, vol. 9, pp. 2787-2794 (Dec. 10, 1998).

Schmelter et al., "Identification and Characterization of a Small Modular domain in the Herpes Simplex Virus Host Shutoff Protein Sufficient for Interaction with VP16", Journal of Virology, vol. 7, No. 4, pp. 2124-2131, (Apr. 1996).

Smibert et al., "Identification and Characterization of the Virion-Induced Host Shutoff Product of Herpes Simplex Gene UL41", Journal of General Virology, vol. 73, pp. 467-470 (1992).

Smibert et al., "Herpes Simplex Virus VP16 Forms a Complex with the Virion Host Shutoff Protein vhs", Journal of Virology, vol. 68, No. 4, pp. 2339-2346 (Apr. 1994).

Sotomayor et al., "Conversion of Tumor-Specific CD4+T-Cell Tolerance to T-Cell Priming through in vivo ligation of CD40", Nature Medicine, vol. 5, No. 7, pp. 780-784 (Jul. 1999).

Spaete et al., "The Herpes Simplex Virus Amplicon: A New Eucaryotic Defective-Virus Cloning-Amplifying Vector", Cell, vol. 30, pp. 295-304 (Aug. 1982).

Spector et al., "Replication-defective Herpesvirus Amplicon Vectors and Their Use for Gene Transfer", Cells: A Laboratory Manual, vol. 2: Light Microscopy and Cell Structure, pp. 91.1-91.10 (1997).

Stavropoulos et al., "An Enhanced Packaging System for Helper-Dependent Herpes Simplex Virus Vectors", Journal of Virology, vol. 72, No. 9, pp. 7137-7143 (Sep. 1998).

Stern et al., "The Oct-1 Homoeodomain Directs Formation of a Multiprotein-DNA Complex with the HSV Transactivator VP16", Nature, vol. 341, pp. 624-630 (Oct. 19, 1989).

Tolba et al., "Development of Herpes Simplex Virus-1 Amplicon-Based Immunotherapy for Chronic Lymphocytic Leukemia", Blood, vol. 98, No. 2, pp. 287-295 (Jul. 15, 2001).

Trojan et al., "Immunoglobulin Framework-Derived Peptides Function as Cytotoxic T-Cell Epitopes Commonly Expressed in B-Cell Malignancies", Nature Medicine, vol. 6, No. 6, pp. 667-672 (Jun. 2000).

Van Kooten et al., "Functions of CD40 on B Cells, Dendritic Cells and other Cells", Immunology, vol. 9, No. 3, pp. 330-337 (Jun. 1997).

Vile et al., "Retroviral Vectors: From Laboratory Tools to Molecular Medicines", Molecular Biotechnology, vol. 5, pp. 139-158 (1996).

Wigdahl et al., "Herpes Simplex Virus Latency in Isolated Human Neurons", Proc. Natl. Acad. Sci. USA, vol. 81, No. 19, pp. 6217-6221,(Oct. 1984).

Wilson et al., "The VP16 Accessory Protein HCF Is a Family of Polypeptides Processed from a Large Precursor Protein", Cell, vol. 74, pp. 115-125 (Jul. 16, 1993).

Xiao et al., "A Cellular Factor Binds to the Herpes Simplex Virus Type 1 Transactivator Vmw65 and Is Required for Vmw65-Dependent Protein-DNA Complex Assembly with Oct-1", Molecular and Cellular Biology vol. 10, No. 9, pp. 4974-4977 (Sep. 1990).

Sun et al., "Improved Titers for Helper Virus-Free Herpes Simplex Virus Type 1 Plasmid Vectors by Optimization of the Packaging Protocol and Addition of Noninfectious Herpes Simplex Virus-Related Particles (Previral DNA Replication Enveloped Particles) to the Packaging Procedure"; *Human Gene Therapy*, vol. 10, No. 12, pp. 2005-2011 (1999).

Zhang et al., "An efficient selection system for packaging herpes simplex virus amplicons"; *Journal of General Virology*, vol. 79, Part 1, pp. 125-131 (1998).

International Search Report dated Jan. 7, 2002 (6 pages).

Bowers, W.J. et al. "Expression of vhs and VP16 during HSV-1 helper virus-free amplicon packaging enhances titers", Gene Therapy, vol. 8, No. 2, pp. 111-120, Jan. 2001.

Bowers, W.J. et al., "Development of integrating HSV-1 amplicon vectors for CNS gene transfer", Society for Neuroscience Abstract, vol. 2002, Abstract No. 387.13, Nov. 2, 2002.

Chen, Xiaowei et al., "HSV amplicon-mediated neurotrophin-3 expression protects murine spiral ganglion neurons from cisplatin-induced damage", Molecular Therapy, vol. 3, No. 6, pp. 958-963, Jun. 6, 2001.

Halterman, M.W. et al., "Restricted replication using VP16 in HSV-1 mutants produces amplicon vectors with reduced toxicity", Society for Neuroscience Abstracts, vol. 26, No. 1-2, Abstract No. 232-13, Nov. 4, 2000.

Johnson, Paul et al., "Improved cell survival by the reduction of immediate-early gene expression in replication-defective mutants of herpes simplex virus type 1 but not by mutation of the virion host shutoff function", Journal of Virology, vol. 68, No. 10, pp. 6347-6362, Oct. 1994.

Holscher et al., "Overexpression of nonconvertible $PrP^c$ $\Delta$114-121 in scrapie-infected mouse neuroblastoma cells leads to trans-dominant inhibition of wild type $PrP^{Sc}$ accumulation," J. Virol. 72(2):1153-9 (1998).

Yant et al., "Somatic integration and long term transgene expression in normal and haemophilia mice using a DNA transposon system," Nat. Gen. 25:35-41 (2000).

* cited by examiner

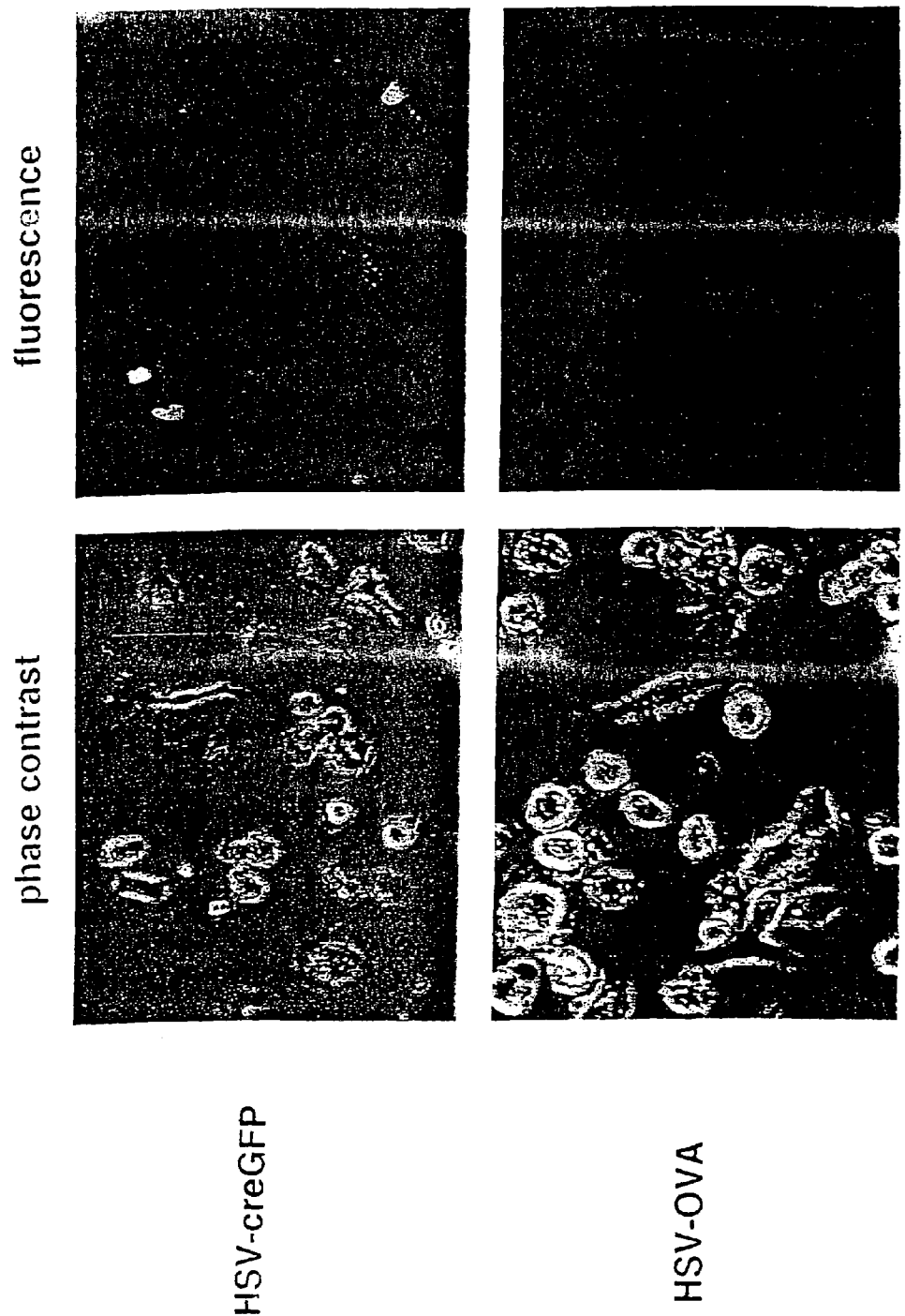
Figure 1: HSV amplicon vector-mediated transduction of murine dendritic cells. Dendritic cells were infected overnight with HSV-creGFP or HSV-OVA amplicons (MOI=1) as a negative control and were directly visualized by fluorescence microscopy without fixation.

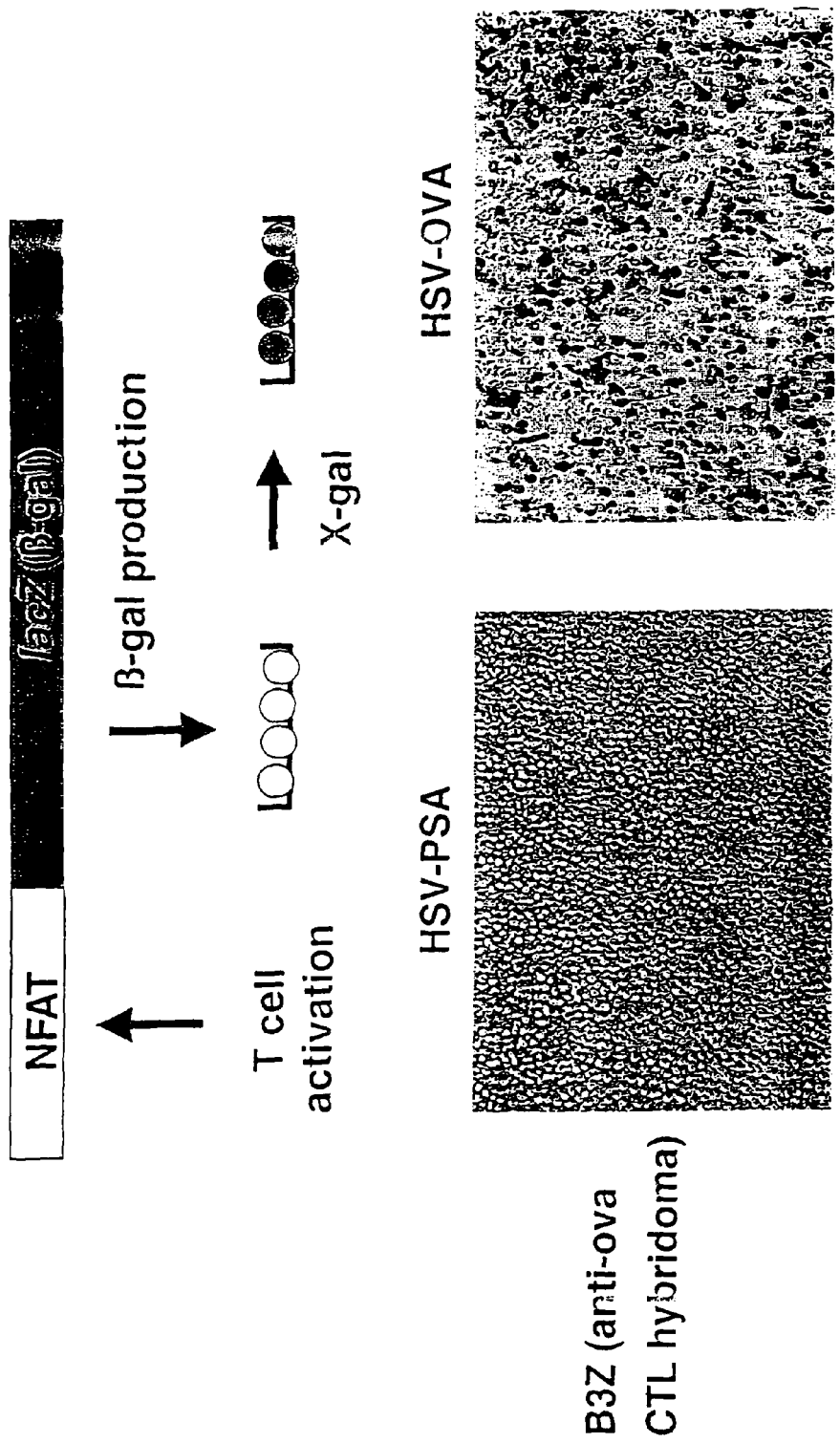

Figure 2: Dendritic cells infected with HSV amplicons present antigen to T cell hybridomas. DCs from a (C57BL/6 x BALB/c1YyJ)F1 mouse were infected with HSV-OVA and cultured overnight with CTL hybridoma B3Z (specific for OVA). These hybridomas have been previously transfected with *lacZ* under control of the IL-2 promoter and can be assayed for activation by staining with X-gal. Blue cells represent activated hybridomas and indicate that the DCs have been transduced and are capable of processing the OVA for class I MHC presentation.

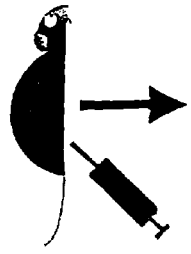 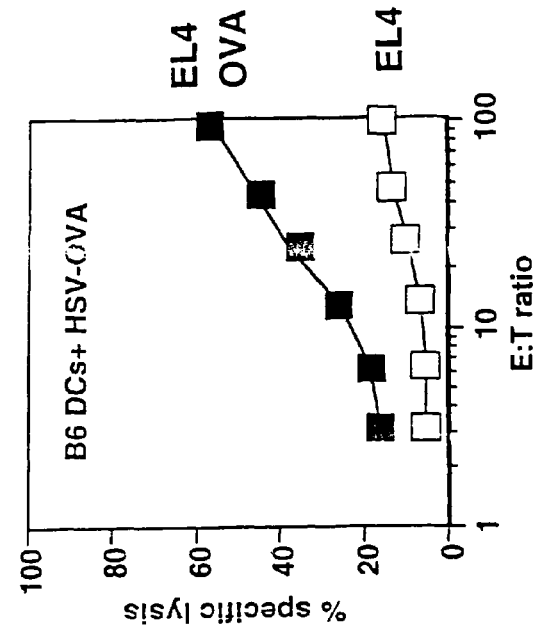

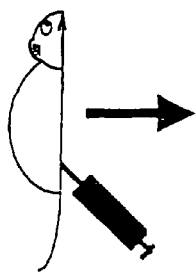 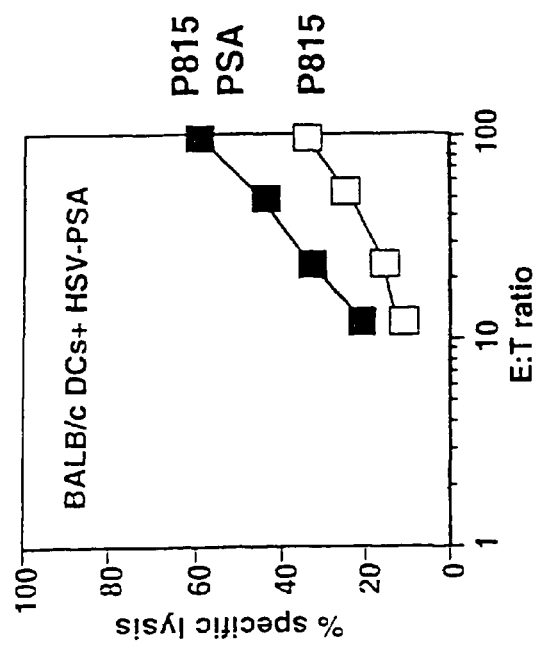

Figure 3: Mice immunized with HSV amplicon-transduced dendritic cells elicit specific cytotoxic T cell responses. Dendritic cells were infected with amplicons at an MOI of 1 and transduced cells were used to immunize mice twice subcutaneously 1 week apart. Splenocytes from immunized animals were re-stimulated *in vitro* for 5 days with irradiated, lipopolysaccharide-treated B cell blasts pulsed with the immunodominant peptide of PSA or OVA. CTL responses were measured using a standard $^{51}$Cr release assay. "E:T ratio" refers to the effector cell to target cell ratio.

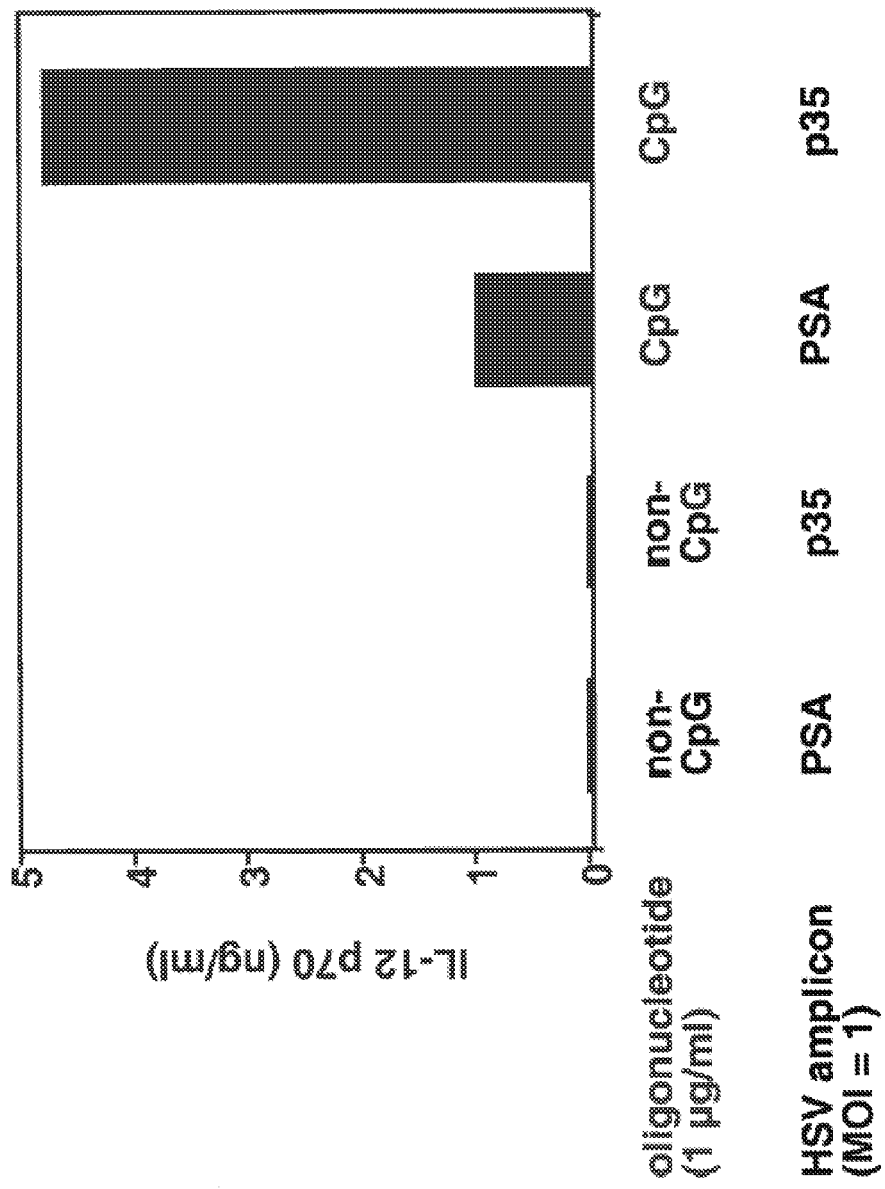

Figure 4: Dendritic cells infected with HSV-p35 amplicons and activated with CpG oligos produce increased levels of IL-12 p70 heterodimer. DCs were infected with HSV amplicons engineered to express the p35 subunit of IL-12, or HSV-OVA amplicons as a control. Cells were then activated overnight with oligonucleotides that contain an immunostimulatory CpG sequence or control oligos in which the CpG sequence is altered to GpC. Supernatants were collected 48 hours later and tested in an IL-12 ELISA specific for IL-12 p70 heterodimer.

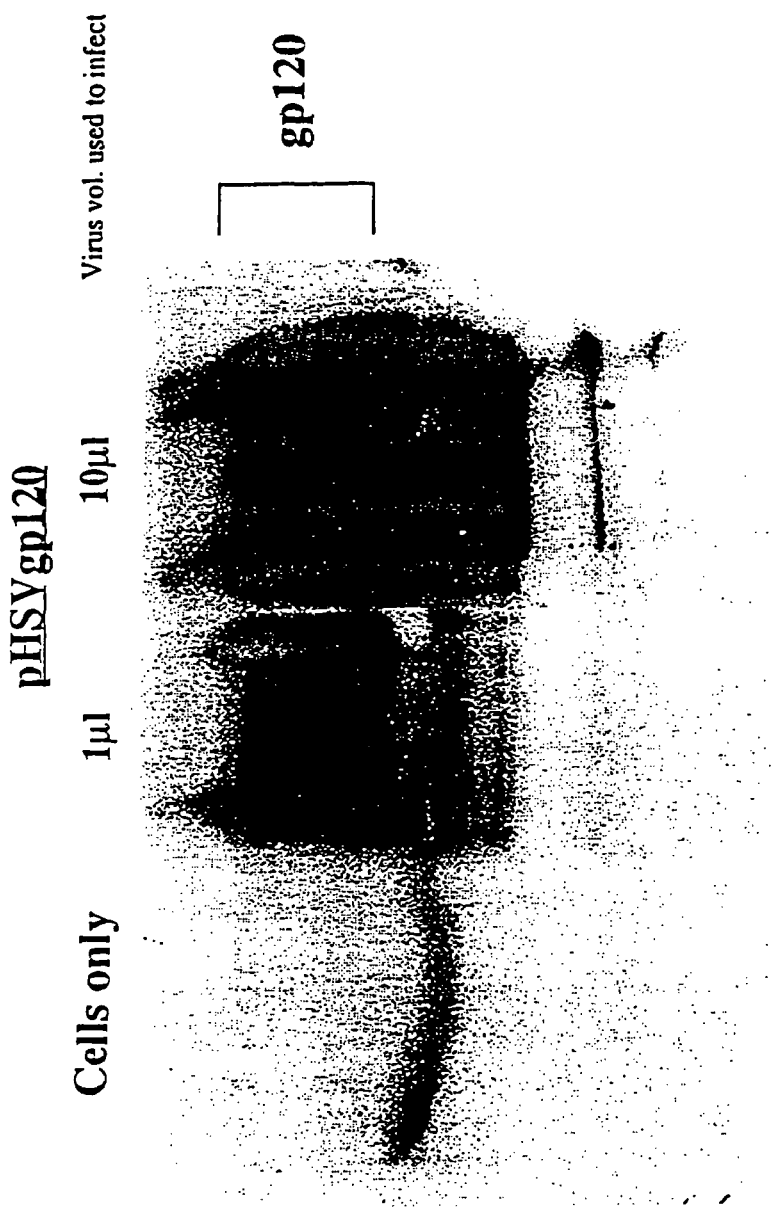

Figure 5: Western blot analysis of lysates prepared from HSVgp120-infected NIH 3T3 cells. A 20-μg sample of cell lysate isolated from uninfected and HSVgp120-infected NIH 3T3 cells were electrophoretically separated on a 10% SDS-PAGE gel, transferred to nylon membrane, and blot incubated with a HIV gp120-specific antibody (Clontech, Inc.). The gp120-specific bands were visualized on film using chemiluminescent detection.

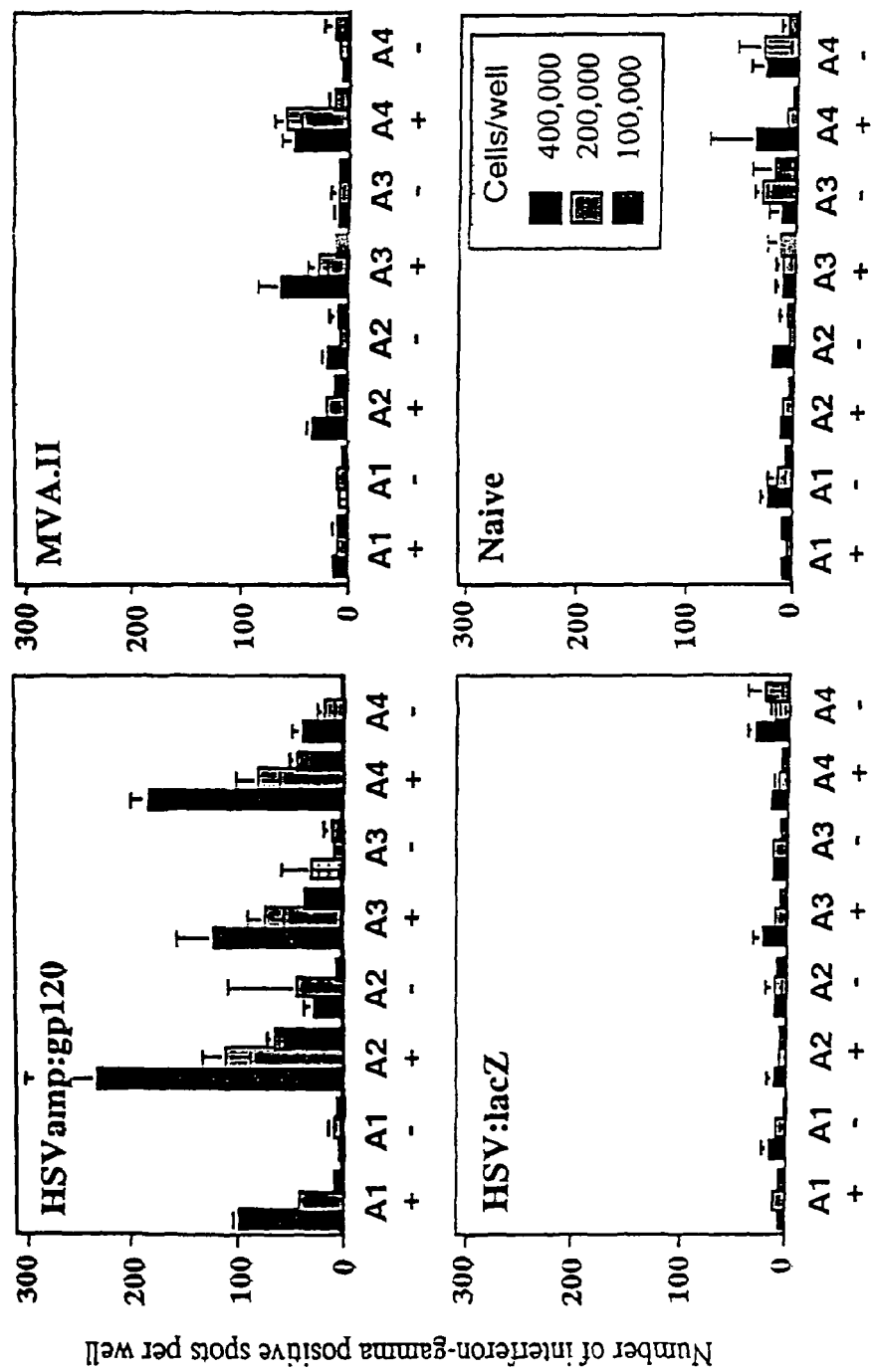

Figure 6: Immunization of mice with HSVgp120 leads to a marked cell-mediated immune response. Cellular responses to the class I-restricted peptide from gp120 (RGPGRAFVTI) were measured by interferon gamma Elispot. Results from triplicate assays are shown, performed with 3 dilutions of input splenocytes. Numbers represent individual animals, with splenocytes incubated with (+) or without (-) the specific peptide. MVA.H represents a positive control (MVA encoding the V3 peptide).

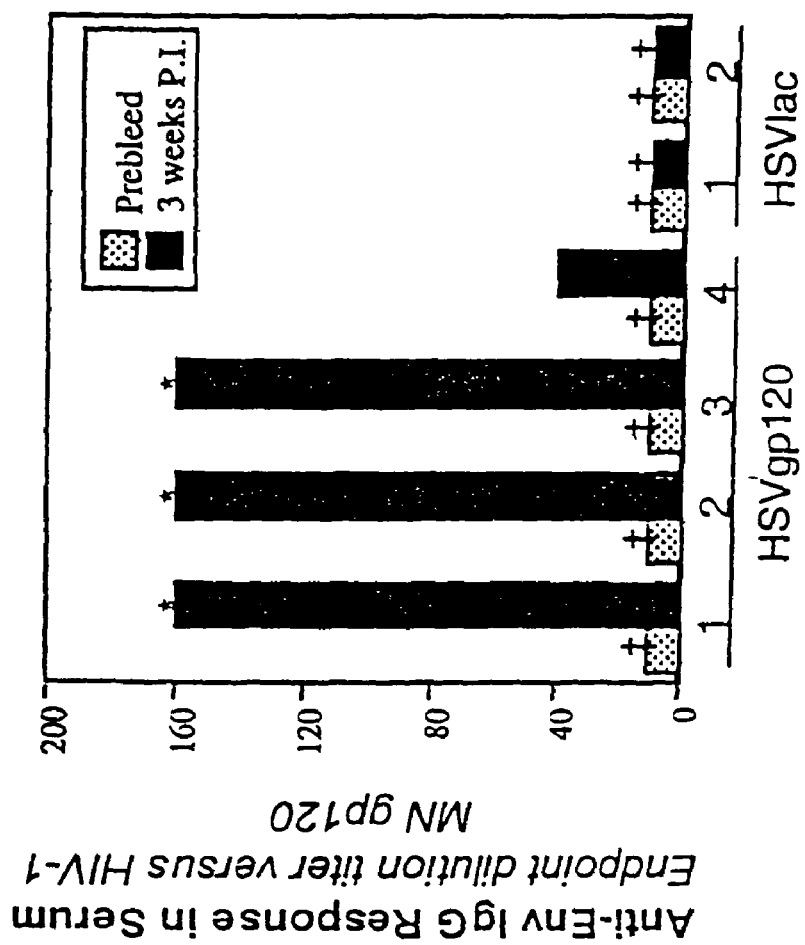
Figure 7: Elicitation of a humoral response in mice immunized with HSVgp120. IgG responses to gp120 were measured in sera from mice before or 3 weeks following infection with HSVgp120. Numbers denote individual animals. HSVlac served as the negative control. "*" denotes titers detected at the 1:160 final dilution and "+" denotes titers determined at the 1:10 dilution.

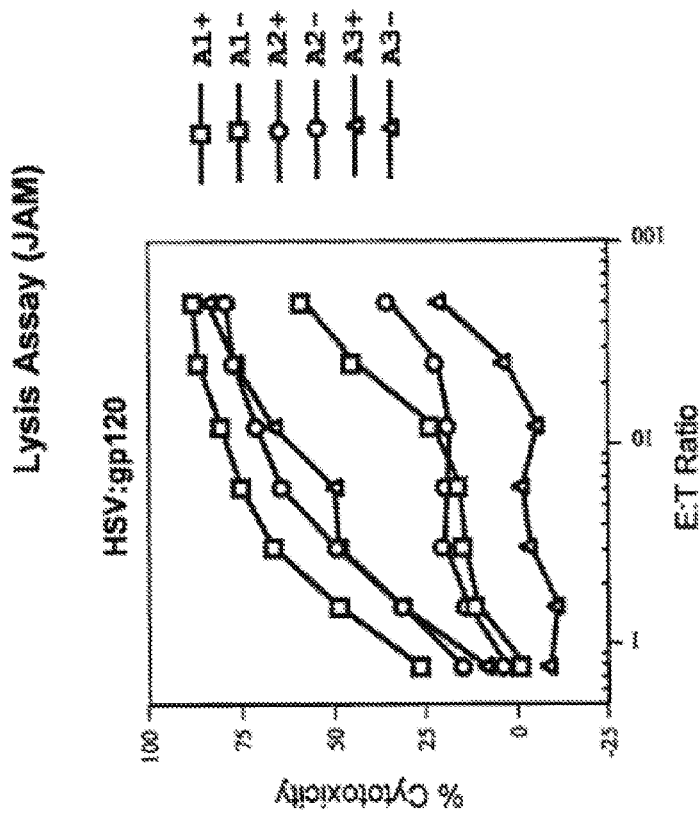

Figure 8. HSVgp120-mediated induction of CTL activity. BALB/c mice were inoculated with HSV:gp120 amplicon (10⁶ pfu) via the intramuscular (IM; thigh) route. Animals were sacrificed 21 days later, and splenocytes harvested. Splenocytes were restimulated in the presence of LPS blasts loaded with the HIVgp120 specific peptide (RGPGRAFVT). After 5 days, these effector cells were then mixed at various ratios with radiolabeled P815 target cells, either pulsed with peptide (+; RGPGRAFVT) or unpulsed (-). Cell killing was assessed using the JAM assay method (Matzinger et al.), and data are expressed in terms of percent cytotoxicity at each effector to target (E:T) ratio. A1, 2, 3 denote data from individual animals. The data show that a single intramuscular inoculation of the HSVgp120 vector led to a strong, peptide-specific, cytotoxic effector response in these animals.

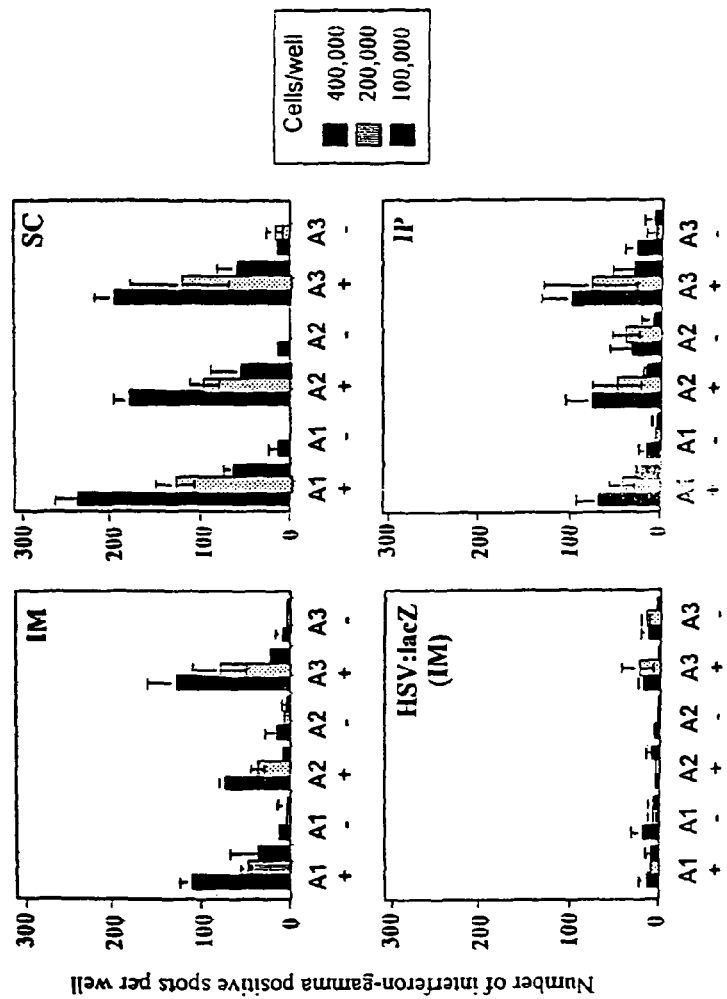

Figure 9. Effect of route of inoculation on immune response. BALB/c mice were inoculated with HSV:gp120 amplicon ($10^6$ pfu) via either intramuscular (IM; thigh), subcutaneous (SC; tail base), or intraperitoneal (IP) routes; control animals received $10^6$ pfu of the HSVlacZ vector via the IM route. Animals were sacrificed 21 days later, and splenocytes harvested. An interferon-gamma Elispot assay was then performed on these splenocytes, using either an HIVgp120 specific peptide (+; RPGRAFVTI) or no peptide (-). A1, 2, 3 denote data from individual animals. See other Elispot assay for additional details. The data show thatsubcutaneous inoculation of the HSVgp120 vector led to the greatest level of cellular immune response in splenocytes, as defined in this assay system under the parameters used.

TABLE 1

Essential HSV-1 Genes

| Gene* | Protein(Function) | Genbank I.D. No. | Accession No.** |
|---|---|---|---|
| UL1 | virion glycoprotein L (gL) | 136775 | CAA32337 |
| UL5 | component of DNA helicase-primase complex | 74000 | CAA32341 |
| UL6 | minor capsid protein | 136794 | CAA32342 |
| UL7 | unknown | 136798 | CAA32343 |
| UL8 | DNA helicase/primase complex associated protein | 136802 | CAA32344 |
| UL8.5 | unknown*** | — | — |
| UL9 | ori-binding protein | 136806 | CAA32345 |
| UL15 | DNA cleavage/packaging protein | 139646 | CAA32330 |
| UL17 | tegument protein | 136835 | CAA32329 |
| UL18 | capsid protein, VP23 | 139191 | CAA32331 |
| UL19 | major capsid protein, VP5 | 137371 | CAA32332 |
| UL22 | virion glycoprotein H, gH | 138515 | CAA32338 |
| UL25 | DNA packaging virion protein | 136863 | CAA32317 |
| UL26 | serine protease, self-cleaves to form VP21 & VP24 | 139233 | CAA32318 |
| UL26.5 | capsid scaffolding protein, VP22a | 1944539 | CAA32319 |
| UL27 | virion glycoprotein B, gB | 138194 | CAA32320 |
| UL28 | DNA cleavage and packaging protein, ICP18.5 | 124088 | CAA32321 |
| UL29 | single-stranded DNA binding protein, ICP8 | 118746 | CAA32322 |
| UL30 | DNA polymerase | 118878 | CAA32323 |
| UL31 | UL34-associated nuclear protein | 136875 | CAA32324 |
| UL32 | cleavage and packaging protein | 136879 | CAA32307 |
| UL33 | capsid packaging protein | 136883 | CAA32308 |
| UL34 | membrane-associated virion protein | 136888 | CAA32309 |
| UL36 | very large tegument protein, ICP1/2 | 138576 | CAA32311 |
| UL37 | tegument protein, ICP32 | 136894 | CAA32312 |
| UL38 | capsid protein, VP19C | 438360 | CAA32313 |
| UL42 | DNA polymerase accessory protein | 136905 | CAA32305 |
| UL48 | alpha trans-inducing factor, VP16 | 114359 | CAA32298 |
| UL49 | putative microtubule-associated protein, VP22 | 136927 | CAA32299 |
| UL49.5 | membrane-associated virion protein | 1944541 | CAA32300 |
| UL52 | component of DNA helicase/primase complex | 136939 | CAA32288 |
| UL54 | regulation and transportation of RNA, ICP27 | 124180 | CAA32290 |
| α4 (RS1) | positive and negative gene regulator, ICP4 | 124141 | CAA32286 |
|  |  |  | CAA32278 |
| US6 | virion glycoprotein D, gD | 73741 | CAA32283 |

*The complete genome of HSV-1 is reported at Genbank Accession No. X14112, which is hereby incorporated by reference in its entirety.
**Each of the listed Accession Nos. which report an amino acid sequence for the encoded proteins is hereby incorporated by reference in its entirety.
***UL8.5 maps to a transcript which overlaps and is in frame with the carboxyl terminal of UL9 (Baradaran et al., "Transcriptional analysis of the region of the herpes simplex virus type 1 genome containing the UL8, UL9, and UL10 genes and identification of a novel delayed-early gene product, OBPC," J. Virol. 68(7):4251–4261 (1994), which is hereby incorporated by reference in its entirety).

Figure 10

UPPER TABLE
OF
FIGURE 11

| Treatment | IL-2 (pg/ml) |
|---|---|
| No virus control | 461 |
| HSVlac | N.D. |
| hf-HSVlac | 54 |
| HSVB7.1 | 173 |
| hf-HSVB7.1 | 1942 |

Table 1: IL-2 production following transduction of CLL cells with helper virus-containing and helper virus-free amplicon stocks N.D.=not detected

MIDDLE TABLE

| Treatment | CD40L (%) | B7.1 (%) | CD40L and B7.1 (%) |
|---|---|---|---|
| HSVlac | 2.0 | 12.5 | 0.5 |
| hf-HSVlac | 1.4 | 16.3 | 0.3 |
| HSVCD40L | 77.4 | 13.1 | 7 |
| hf-HSVCD40L | 48.6 | 41.6 | 14.7 |

Table 2: Percentage of CLL cells expressing B7.1 and CD40L following transduction with helper virus-containing and helper virus-free amplicon stocks.

LOWER TABLE

| Treatment | γ-interferon (pg/ml) |
|---|---|
| No virus control | 515 |
| hf-HSVlac | 550 |
| hf-HSVCD40L | 1088 |

Table 3: γ-interferon levels in supernatant derived from CTL assay using CLL cells transduced with helper virus-free amplicon stocks

SEQUENCE LISTING

```
<160> NUMBER OF SEQ ID NOS: 16

<210> SEQ ID NO 1
<211> LENGTH: 9
<212> TYPE: PRT
<213> ORGANISM: Human immunodeficiency virus

<400> SEQUENCE: 1

Arg Gly Pro Gly Arg Ala Phe Val Thr
1               5

<210> SEQ ID NO 2
```

```
<211> LENGTH: 35
<212> TYPE: DNA
<213> ORGANISM: Artificial Sequence
<220> FEATURE:
<223> OTHER INFORMATION: oligonucleotide for PCR

<400> SEQUENCE: 2
cggaattccg caggttttgt aatgtatgtg ctcgt                        35

<210> SEQ ID NO 3
<211> LENGTH: 38
<212> TYPE: DNA
<213> ORGANISM: Artificial Sequence
<220> FEATURE:
<223> OTHER INFORMATION: oligonucleotide for PCR

<400> SEQUENCE: 3
ctccgaagct taagcccgat atcgtctttc ccgtatca                     38

<210> SEQ ID NO 4
<211> LENGTH: 22
<212> TYPE: DNA
<213> ORGANISM: Artificial Sequence
<220> FEATURE:
<223> OTHER INFORMATION: oligonucleotide for PCR

<400> SEQUENCE: 4
accccgtacg tcttcccgag cg                                      22

<210> SEQ ID NO 5
<211> LENGTH: 22
<212> TYPE: DNA
<213> ORGANISM: Artificial Sequence
<220> FEATURE:
<223> OTHER INFORMATION: oligonucleotide for PCR

<400> SEQUENCE: 5
gggatctgcc attgtcagac at                                      22

<210> SEQ ID NO 6
<211> LENGTH: 22
<212> TYPE: DNA
<213> ORGANISM: Artificial Sequence
<220> FEATURE:
<223> OTHER INFORMATION: oligonucleotide for PCR

<400> SEQUENCE: 6
tgctggcacc agacttgccc tc                                      22

<210> SEQ ID NO 7
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 7
cggctaccac atccaaggaa                                         20

<210> SEQ ID NO 8
<211> LENGTH: 18
<212> TYPE: DNA
<213> ORGANISM: Artificial Sequence
<220> FEATURE:
<223> OTHER INFORMATION: oligonucleotide for PCR

<400> SEQUENCE: 8
```

-continued

```
gctggaatta ccgcggct                                                      18

<210> SEQ ID NO 9
<211> LENGTH: 22
<212> TYPE: DNA
<213> ORGANISM: Artificial Sequence
<220> FEATURE:
<223> OTHER INFORMATION: oligonucleotide for PCR

<400> SEQUENCE: 9
caggaccact tctgcgctcg gc                                                 22

<210> SEQ ID NO 10
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 10
ctggatggag gcggataaag t                                                  21

<210> SEQ ID NO 11
<211> LENGTH: 22
<212> TYPE: DNA
<213> ORGANISM: Artificial Sequence
<220> FEATURE:
<223> OTHER INFORMATION: oligonucleotide for PCR

<400> SEQUENCE: 11
tgctggcacc agacttgccc tc                                                 22

<210> SEQ ID NO 12
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 12
tggtgtgggc cataattcaa                                                    20

<210> SEQ ID NO 13
<211> LENGTH: 10
<212> TYPE: PRT
<213> ORGANISM: Human immunodeficiency virus

<400> SEQUENCE: 13

Arg Gly Pro Gly Arg Ala Phe Val Thr Ile
 1               5                  10

<210> SEQ ID NO 14
<211> LENGTH: 9
<212> TYPE: PRT
<213> ORGANISM: Human immunodeficiency virus

<400> SEQUENCE: 14

Arg Gly Pro Arg Ala Phe Val Thr Ile
 1               5

<210> SEQ ID NO 15
<211> LENGTH: 9
<212> TYPE: PRT
<213> ORGANISM: Human immunodeficiency virus

<400> SEQUENCE: 15
```

```
Arg Pro Gly Arg Ala Phe Val Thr Ile
 1               5
```

```
<210> SEQ ID NO 16
<211> LENGTH: 9
<212> TYPE: DNA
<213> ORGANISM: Artificial Sequence
<220> FEATURE:
<223> OTHER INFORMATION: Synthetically generated oligonucleotide

<400> SEQUENCE: 16 taatgarat                                                              9
```

HELPER VIRUS-FREE HERPESVIRUS AMPLICON PARTICLES AND USES THEREOF

RELATED APPLICATIONS

This application is a continuation of U.S. Ser. No. 09/997,848, filed Nov. 29, 2001, now abandoned, which claims the benefit of U.S. Ser. No. 60/250,079, filed Nov. 30, 2000, and U.S. Ser. No. 60/253,858, filed Nov. 29, 2000. The contents of these applications are hereby incorporated by reference in the present application in their entirety.

STATEMENT REGARDING GOVERNMENT SUPPORT

The work described herein was funded, in part, by grants from the National Institutes of Health. The government may, therefore, have certain rights in the invention.

FIELD OF THE INVENTION

The present invention related to improved methods for making helper virus-free preparations of herpesvirus amplicon particles; the particles per se; and methods of using the particles to treat patients, including patients who have cancer or an infectious disease.

BACKGROUND

Herpes simplex virus (HSV) is a DNA virus capable of rapidly and efficiently infecting a wide variety of cell types (Leib and Olivo, *BioEssays* 15:547-554, 1993). Plasmid-based viral vectors derived from HSV, termed amplicons, are easy to construct and package into viral particles.

SUMMARY

The compositions and methods of the present invention are based on a number of discoveries, including the discoveries that: (1) cells transduced with HSV amplicon vectors can process proteins encoded by the vectors for class I MHC presentation; (2) when used to deliver a viral antigen, herpes virus-based amplicon vectors can induce a cell-mediated immune response that is equivalent to that induced by live herpesvirus vectors and that exceeds that induced by a modified vaccinia Ankara vector; (3) animals immunized with HSV amplicon-transduced dendritic cells respond by producing antigen-specific cytotoxic T lymphocytes (e.g., animals immunized with an HSV-gp120 amplicon display a cell-mediated immune response); (4) animals infected with HSV-gp120 also exhibit a humoral immune response; (5) the expression of virion host shutoff (vhs) proteins in helper virus-free packaging systems improves amplicon titer and vector stocks prepared in this way do not exhibit the pseudotransduction phenomenon (to further enhance packaging efficiency, an HSV transcriptional activator can be introduced into packaging cells); and (6) helper virus-free amplicon preparations are superior to helper virus-containing amplicon preparations (see the studies below).

Accordingly, the invention features new helper virus-free methods for making herpesvirus amplicon particles that can be used in immunotherapies, including those for treating any number of infectious diseases and cancers (including chronic lymphocytic leukemia, other cancers in which blood cells become malignant, lymphomas (e.g. Hodgkin's lymphoma or non-Hodgkin's type lymphomas), melanoma, glioblastoma, astrocytoma, pancreatic cancer, a cancer of the reproductive system, a cancer of the endocrine system, neuroblastoma, breast cancer, colorectal cancer, stomach cancer, cancer of the throat or mouth, lung cancer, or bladder cancer). The invention features: methods of making helper virus-free HSV amplicon particles; cells that contain those particles (e.g., packaging cell lines or patients' cells, infected in vivo or ex vivo); particles produced according to those methods (such particles, regardless of the method by which they are produced, may be abbreviated herein as "hf-HSV" particles); and methods of treating a patient with an hf-HSV particle made according to those methods. For example, hf-HSV particles (including those made according to the methods described herein) that contain one or more genes encoding one or more therapeutic proteins, can be used to transduce cells. For example, one can transduce cells that contain an infectious agent (such as a virus or bacterium) or that have become malignant (e.g., malignant cells of the prostate, skin, bladder, breast, endocrine system, or gastrointestinal tract). The therapeutic protein (discussed further below) can be an immunostimulatory protein and may be a neoantigen (e.g., a tumor-specific antigen, such as prostate-specific antigen (PSA))

In one embodiment, a cell that contains an infectious agent or a cell that is malignant is transduced (in vivo or ex vivo) with an hf-HSV amplicon particle that encodes an immunostimulatory protein (i.e., any immunomodulatory protein or peptide that, when expressed by a target cell, induces or enhances an immune response to that cell). For example, a patient who has cancer can be treated with an HSV amplicon particle (or a cell within which it is contained) that expresses a protein that acts as a general stimulator of the immune system or a specific protein, such as a tumor-specific antigen (these particles and cells can be those made by the methods described herein). Similarly, a patient who has an infectious disease can be treated with an HSV amplicon particle (or a cell within which it is contained) that expresses a protein that acts as a general stimulator of the immune system or a specific antigen associated with (i.e., expressed by) the infectious agent (here again, the patients that are treated for an infectious disease can be treated with particles or cells made by the methods described herein).

Immunostimulatory proteins include cytokines, including chemotactic cytokines (also known as chemokines) and interleukins, adhesion molecules (e.g., I-CAM) and costimulatory factors necessary for activation of B cells or T cells.

The hf-HSV particles can be made according to methods known in the art (Applicants know of no suggestion that any previously made particles or cells should be used for the treatment of cancer or infectious disease) or according to the new methods described below (the novel methods for producing herpesvirus amplicon particles produce particles that are different from those produced to date, even those produced by helper virus-free methods, and these particles (and the cells that contain them) can be used to treat not only cancer and infectious disease, but also any condition that would benefit from the administration of a protein (e.g., neurological conditions in which neurotransmitters are not adequately available).

More specifically, the invention features a method of generating a herpesvirus amplicon particle. In one embodiment, the method comprises: (1) providing a cell that has been stably transfected with a nucleic acid sequence that encodes an accessory protein (alternatively, a transiently transfected cell can be provided); and (2) transfecting the cell with (a) one or more packaging vectors that, individually or collectively, encode one or more HSV structural proteins but do not encode a functional herpesvirus cleavage/packaging site and (b) an amplicon plasmid comprising a sequence that encodes a functional herpesvirus cleavage/packaging site and a herpesvirus origin of DNA replication. In another embodiment, the method comprises transfecting a cell with (a) one or more packaging vectors that, individually or collectively, encode one or more HSV structural proteins but do not encode a functional herpesvirus cleavage/packaging site; (b) an amplicon plasmid comprising a sequence that encodes a functional herpesvirus cleavage/packaging site, a herpesvirus origin of DNA replication, and a sequence that encodes an immunomodulatory protein, a tumor-specific antigen, or an antigen of an infectious agent; and (c) a nucleic acid sequence that encodes an accessory protein.

In either of these methods, one or more of the following additional limitations may apply. For example, in either method, the herpesvirus can be any of the more than 100 known species of herpesvirus. For example, the herpesvirus can be an alpha herpesvirus (e.g., a Varicella-Zoster virus, a pseudorabies virus, or a herpes simplex virus (e.g., type 1 or type 2 HSV) or an Epstein-Barr virus. Similarly, both methods require sequences that encode an accessory protein and, in either method, the accessory protein can be a protein that inhibits the expression of a gene in the cell. For example, the accessory protein can be a virion host shutoff (vhs) protein (e.g., an HSV-1 vhs protein, an HSV-2 vhs protein, an HSV-3 vhs protein, bovine herpesvirus 1 vhs protein, bovine herpesvirus 1.1 vhs protein, gallid herpesvirus 1 vhs protein, gallid herpesvirus 2 virion hsp, suid herpesvirus 1 vhs protein, baboon herpesvirus 2 vhs protein, pseudorabies vhs protein, cercopithecine herpesvirus 7 vhs protein, meleagrid herpesvirus 1 vhs protein, equine herpesvirus 1 vhs protein, or equine herpesvirus 4 vhs protein). Any of these proteins can be operatively coupled to its native transcriptional control element(s) or to an artificial control element (i.e., a control element that does not normally regulate its expression in vivo).

The methods by which herpesvirus amplicon particles are generated can also include a step in which the cell is transfected with a sequence encoding a VP16 protein, which may be transiently or stably expressed. Alternatively, or in addition, one can engineer a transcriptional activator to mimic VP16 (e.g., a pseudo-activator that recognizes cis elements but uses a different transcriptional activation domain).

The VP16 protein can be HSV1 VP16, HSV-2 VP16, bovine herpesvirus 1 VP16, bovine herpesvirus 1.1 VP 16, gallid herpesvirus 1 VP 16, gallid herpesvirus 2 VP 16, meleagrid herpesvirus 1 VP16, or equine herpesvirus 4 VP16.

The vhs and VP16 encoding sequences can be introduced into a cell on the same vector or on two different vectors or on two different types of vectors (e.g., both sequences can be introduced in the same plasmid, in two different plasmids, or in a plasmid and cosmid). Sequences encoding vhs and/or VP16 can be transiently or stably introduced into cells (these methods are routine in the art), and the invention features a cell that is transiently or stably transfected with one or both of the sequences that encode one or more of a vhs or VP16 protein.

As noted above, the herpesvirus (e.g., HSV) amplicon particles are made by methods that employ one or more packaging vectors, which may comprise a cosmid (and may include a set of cosmids), a yeast artificial chromosome, a bacterial artificial chromosome, a human artificial chromosome, or an F element plasmid. A single packaging vector can encode the entire genome of a herpesvirus, or the genome may be divided between two or more vectors. For example, the packaging vectors can include a set of cosmids (e.g., a set of cosmids comprising cos 6Δa, cos 28, cos 14, cos 56, and cos 48Δa).

One or more packaging vectors, individually or collectively, can express the structural herpesvirus proteins. The herpesvirus origin of DNA replication is not present in the one or more packaging vectors.

In the method first described above (the method that employs a transiently or stably transfected cell), the amplicon plasmid can also include a sequence encoding a therapeutic agent. The therapeutic agent can be a protein or an RNA molecule (e.g., an antisense RNA molecule, RNAi, or a ribozyme). In the event the therapeutic agent is a protein, the protein can be a receptor (e.g., a receptor for a growth factor or neurotransmitter), a signaling molecule (e.g., a growth factor or neurotransmitter), a transcription factor, a factor that promotes or inhibits apoptosis, a DNA replication factor, an enzyme, a structural protein, a neural protein, or a histone. The protein can also be an immunomodulatory protein (e.g., a cytokine, such as an interleukin, an interferon, or a chemokine, or a costimulatory molecule, such as a B7 molecule or CD40L), a tumor-specific antigen (e.g., PSA), or an antigen of an infectious agent (e.g., a virus such as a human immunodeficiency virus, a herpesvirus, a papillomavirus, an influenza virus, or Ebola virus, a bacterium (e.g., an *Escherichia* (e.g., *E. coli*) *Staphylococcus, Campylobacter* (e.g., *C. jejuni*), *Listeria* (e.g., *L. monocytogenes*), *Salmonella, Shigella* or *Bacillus* (e.g., *Bacillus anthracis*)), or a parasite.

In the second method described above, the amplicon plasmid encodes an immunomodulatory protein, a tumor-specific antigen, or the antigen of an infectious agent (including those described above). It will be apparent to one of ordinary skill in the art which therapeutic agents can be expressed to generate particles and cells useful for treating which conditions. For example, one would select an antigen expressed by HIV (e.g., gp120) to treat a patient who is infected, or who may become infected, with HIV.

The amplicon plasmid can include a promoter to increase the efficiency of expression of the therapeutic agent.

In addition, the invention features kits containing one or more of the herpesvirus amplicon particles described herein; one of more of the cells containing them; or one or more of the components useful in generating either the particles or the cells. For example, a kit can include a packaging vector and an amplicon plasmid. Optionally, the kit can also contain stably transfected cells. Optionally, the kit can include instructions for use.

The particles generated by the methods of the invention, and cells that contain those particles, are also within the scope of the invention. The particles and cells that come within the scope of the invention include any of those made using the methods described herein. The cell can be virtually any differentiated cell, including a neuron, a blood cell, a hepatocyte, a keratinocyte, a melanocyte, a neuron, a glial cell, an endocrine cell, an epithelial cell, a muscle cell, a prostate cell, or a testicular cell. The cell can also be a malignant cell (including any of those that arise from the differentiated cells just listed; e.g., a neuroblastoma, a lymphoma or leukemia cell, a hepatocarcinoma cell etc.). Alternatively, or in addition, the cell can be any cell that is infected with an infectious agent (including a virus, a bacterium, or a parasite, including, but not limited to, those types described herein).

Gene therapy vectors based on the herpes simplex virus have a number of features that make them advantageous in gene therapies. They exhibit a broad cellular tropism, they have the capacity to package large amounts of genetic material (and thus can be used to express multiple genes or gene sequences), they have a high transduction efficiency, and they are maintained episomally, which makes them less prone to insertional mutagenesis. In addition to infecting many different types of cells, HSV vectors can transduce non-replicating or slowly replicating cells, which has therapeutic advantages. For example, freshly isolated cells can be transduced in tissue culture, where conditions may not be conducive to cell replication. The ability of HSV vectors to infect non-replicating or poorly replicating cells also means that cells (such as tumor cells) that have been irradiated can still be successfully treated with HSV vectors.

The transduction procedure can also be carried out fairly quickly; freshly harvested human tumors have been successfully transduced within about 20 minutes. As a result, cells (such a tumor cells) can be removed from a patient, treated, and readministered to the patient in the course of a single operative procedure (one would readminister tumor cells following transduction with, for example, an immunostimulatory agent (HSV vectors encoding immunomodulatory proteins and cells transduced with such vectors can confer specific antitumor immunity that protects against tumor growth in vivo).

On the other hand, it is inherently difficult to manipulate a large viral genome (150 kb) and HSV-encoded regulatory and structural viral proteins may be toxic (Frenkel et al., *Gene Ther.* 1 Suppl. 1:S40-46, 1994).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. All publications, patent applications, patents, and other references mentioned herein are incorporated by reference in their entirety. In case of conflicting subject matter, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is a panel of four photomicrographs. Murine dendrite cells were photographed using phase contrast optics and fluorescent light after infection with HSV-creGFP or HSV-OVA amplicons (MOI=1).

FIG. 2 is a schematic representation of an infection procedure and photographs of activated T cells following co-culture with infected dendritic cells.

FIG. 3 is a schematic representation of an immunization and line graphs of the resulting cytotoxic T lymphocyte (CTL) response.

FIG. 4 is a bar graph representing the expression of IL-12 p70 (ng/ml) following treatment of dendritic cells (antigen presenting cells (APCs)) with one of two HSV amplicons (one that expresses PSA and one that expresses p35) followed by activation with oligonucleotides that contain an immunostimulatory CpG sequence or oligonucleotides in which the CpG sequence is altered to GpC.

FIG. 5 is a photograph of a Western blot. Lysates were prepared from HSVgp120-infected NIH 3T3 cells.

FIG. 6 is a series of four bar graphs illustrating the cellular responses to class I-restricted peptides from gp120 (RG-PGRAFVTI is represented by SEQ ID NO:13).

FIG. 7 is a bar graph made by analyzing the humoral response in mice immunized with HSVgp120 (anti-env IgG responses in serum).

FIG. 8 is a graph plotting the results of a cell lysis assay (JAM). HSVgp120 mediated induction of CTL activity (RG-PRAFVTI is represented by SEQ ID No:14).

FIG. 9 is a series of four bar graphs illustrating the effect of administering an HSV-gp120 amplicon by three common routes of administration (intramuscular, subcutaneous, or intraperitoneal; RPGRAFVTI is represented by SEQ ID NO: 15).

FIG. 10 is a Table of essential HSV-1 genes.

FIG. 11 shows three Tables. The uppermost concerns IL-2 production following transduction of CLL cells with helper virus-containing and helper virus-free amplicon stocks; the middle table concerns the % of CLL cells expressing B7.1 and CD40L following transduction with helper virus-containing and helper virus-free amplicon stocks; the lower table concerns gamma-interferon levels in supernatant derived from CTL assays using CLL cells transduced with helper virus-free amplicon stocks.

DETAILED DESCRIPTION

Helper virus-free systems for packaging herpesvirus particles, including those described herein, include the use of at least one vector (herein, the packaging vector) that, upon delivery to a cell that supports herpesvirus replication, will form a DNA segment (or segments) capable of expressing sufficient structural herpesvirus proteins that they are capable of assembling into herpesvirus particles. For example, sets of cosmids have been isolated that contain overlapping clones that represent the entire genomes of a variety of herpesviruses (see U.S. Pat. No. 5,998,208). The packaging vectors are prepared so that none of the viruses used will contain a functional herpesvirus cleavage-packaging site containing sequence. This sequence is referred to as the "a" sequence (and is not encoded by the packaging vector(s)). The "a" sequence can be deleted from the packaging vector(s) by any of a variety of techniques practiced by those of ordinary skill in the art. For example, one can simply delete the entire sequence (by, for example, the techniques described in U.S. Pat. No. 5,998,208). Alternatively, one can delete a sufficient portion of the sequence to render it incapable of packaging. Another alternative is to insert nucleotides into the site that render it non-functional.

The core of the herpesvirus particle is formed from a variety of structural genes that create the capsid matrix. It is necessary to have those genes for matrix formation present in a susceptible cell used to prepare particles. Preferably, the necessary envelope proteins are also expressed. In addition, there are a number of other proteins present on the surface of a herpesvirus particle. Some of these proteins help mediate viral entry into certain cells. Thus, the inclusion or exclusion of the functional genes encoding these proteins will depend upon the particular use of the particle.

The amplicon plasmid contains a herpesvirus cleavage/packaging site containing sequence and an origin of DNA replication (ori) that is recognized by the herpesvirus DNA replication proteins and enzymes. This vector permits packaging of desired nucleotide inserts in the absence of helper viruses. In some embodiments, the amplicon plasmid contains at least one heterologous DNA sequence that encodes a therapeutic agent, optionally and operatively linked to a promoter sequence.

Herpesvirus (e.g., HSV)-based vectors have several features that make them attractive for use in gene therapies. As noted above, they transduce cells in a highly efficient manner, they can infect post-mitotic cells, and they have the ability to package large amounts of genetic material. The amplicon plasmid, essentially a eukaryotic expression plasmid, can contain one or more of the following elements: (i) an HSV-derived origin of DNA replication (ori) and packaging sequence ("a" sequence); (ii) a transcription unit driven typically the the HSV-1 immediate early (IE) 4/5 promoter followed by an SV-40 polyadenylation site; and (iii) a bacterial origin of replication and an antibiotic resistance gene for propagation in *E. coli* (Frenkel, supra; Spaete and Frenkel, *Cell* 30:295-304, 1982).

Amplicon plasmids are dependent upon helper virus function to provide the replication machinery and structural proteins necessary for packaging amplicon plasmid DNA into viral particles. Helper packaging function is usually provided by a replication-defective virus that lacks an essential viral regulatory gene. The final product of helper virus-based packaging contains a mixture of varying proportions of helper and amplicon virions. Recently, helper virus-free amplicon packaging methods were developed by providing a packaging-deficient helper virus genome via a set of five overlapping cosmids (Fraefel et al., *J. Virol.* 70:7190-7197, 1996) or by using a bacterial artificial chromosome (BAC) that encodes for the entire HSV genome minus its cognate cleavage/packaging signals (Stavropoulos and Strathdee, *J. Virol.* 72:7137-7143, 1998; Saeki et al., *Hum Gene Ther.* 9:2787-2794, 1998).

Conditions Amenable to Treatment

The compositions of the present invention (including herpesvirus particles and cells that contain them) can be used to treat patients who have been, or who may become, infected with a wide variety of agents (including viruses such as a human immunodeficiency virus, human papilloma virus, herpes simplex virus, influenza virus, pox viruses, bacteria, such as *E. coli* or a *Staphylococcus*, or a parasite) and with a wide variety of cancers. A patient can be treated after they have been diagnosed as having a cancer or an infectious disease or, since the agents of the present invention can be formulated as vaccines, patients can be treated before they have developed cancer or contracted an infectious disease. Thus, "treatment" encompasses prophylactic treatment.

Chronic lymphocytic leukemia (CLL) is a malignancy of mature appearing small B lymphocytes that closely resemble those in the mantle zone of secondary lymphoid follicles (Caligaris-Cappio and Hamblin, *J. Clin. Oncol.* 17:399-408, 1999). CLL remains a largely incurable disease of the elderly with an incidence of more than 20 per 100,000 above the age of 70, making it the most common leukemia in the United States and Western Europe. CLL, which arises from an antigen-presenting B cell that has undergone a non-random genetic event (del13q14-23.1, trisomy 12, del 11q22-23 and del6q21-23 (Dohner et al., *J. Mol. Med.* 77:266-281, 1999) and clonal expansion, exhibits a unique tumor-specific antigen in the form of surface immunoglobulin. CLL cells possess the ability to successfully process and present this tumor antigen, a characteristic that makes the disease an attractive target for immunotherapy (Bogen et al., *Eur. J. Immunol.* 16:1373-1378, 1986; Bogen et al., *Int. Rev. Immunol.* 10:337-355, 1993; Kwak et al., *N. Engl. J. Med.* 327:1209-1215, 1992; and Trojan et al., *Nat. Med.* 6:667-672, 2000). However, the lack of expression of co-stimulatory molecules on CLL cells renders them inefficient effectors of T cell activation, a prerequisite for generation of anti-tumor immune responses (Hirano et al., *Leukemia* 10:1168-1176, 1996). This failure to activate T cells has been implicated in the establishment of tumor-specific tolerance (Cardoso et al., *Blood* 88:41-48, 1996). Reversal of preexisting tolerance can, potentially, be achieved by up-regulating a panel of co-stimulatory molecules (B7.1, B7.2 and ICAM-I) (Grewal and Flavell, *Immunol. Rev.* 153:85-106, 1996) through the activation of CD40 receptor-mediated signaling and concomitant enhancement of antigen presentation machinery (Khanna et al., *J. Immunol.* 159:5982-5785, 1997; Lanzavecchia, *Nature* 393:413-414, 1998; Diehl et al., *Nat. Med.* 5:774-779, 1999; Sotomayor et al., *Nat. Med.* 5:780-787, 1999).

Applying the information above in effective gene therapies for CLL has been hampered by the lack of a safe and reliable vector that can be used to transduce primary leukemia cells. In contrast to tumor cell lines, CLL cells are effectively post-mitotic; only a small fraction of the population enters the cell cycle (Andreeff et al., *Blood* 55:282-293, 1980). Although both retroviral and adenoviral vectors have been employed in different clinical trials for cancer gene therapy, both systems exhibit limitations (Uckert and Walther, *Pharmacol. Ther.* 63:323-347, 1994; Vile et al., *Mol. Biotechnol.* 5:139-158, 1996; Collins, *Ernst Schering Research Foundation Workshop,* 2000; Hitt et al., *Adv. Pharmacol.* 40:137-206, 1997; Kochanek, *Hum. Gene Ther.* 10:2451-2459, 1999). For example, the low levels of integrin receptors for adenovirus on CLL cells mandates the use of very high adenovirus titers, preactivation of the CLL cell with IL-4 and/or anti-CD40/CD40L (Cantwell et al., *Blood* 88:4676-4683, 1996; Huang et al., *Gene Ther.* 4:1093-1099, 1997), or adenovirus modification with polycations to achieve clinically meaningful levels of transgene expression (Howard et al., *Leukemia* 13:1608-1616, 1999).

In some of the Examples below, HSV amplicon particles were used to transduce primary human B-cell chronic lymphocytic leukemia (CLL) cells. The vectors were constructed to encode β-galactosidase (by inclusion of the lacZ gene), B7.1 (also known as CD80), or CD40L (also known as CD154), and they were packaged using either a standard helper virus (HSVlac, HSVB7.1, and HSVCD40L) or by a helper virus-free method (hf-HSVlac, hf-HSVB7.1, and hf-HSVCD40L). CLL cells transduced with these vectors were studied for their ability to stimulate allogeneic T cell proliferation in a mixed lymphocyte tumor reaction (MLTR). A vigorous T cell proliferative response was obtained using cells transduced with hf-HSVB7.1 but not with HSVB7.1. CLL cells transduced with either HSVCD40L or hf-HSVCD40L were also compared for their ability to up-regulate resident B7.1 and function as T cell stimulators. Significantly enhanced B7.1 expression was seen in response to CD40L delivered by hf-HSVCD40L amplicon stock (compared to HSVCD40L). CLL cells transduced with hf-HSVCD40L were also more effective at stimulating T cell proliferation than those transduced with HSVCD40L stocks. These studies support the conclusion that HSV amplicons are efficient vectors for gene therapy, particularly of hematologic malignancies, and that helper virus-free amplicon preparations are better suited for use in therapeutic compositions.

Therapeutic Agents

As noted, the hf-HSV amplicon particles described herein (and the cells that contain them) can express a heterologous protein (i.e., a full-length protein or a portion thereof (e.g., a functional domain or antigenic peptide) that is not naturally encoded by a herpesvirus). The heterologous protein can be any protein that conveys a therapeutic benefit on the cells in which it, by way of infection with an hf-HSV amplicon particle, is expressed or a patient who is treated with those cells.

The therapeutic agents can be immunomodulatory (e.g., immunostimulatory) proteins (as described in U.S. Pat. No. 6,051,428). For example, the heterologous protein can be an interleukin (e.g., IL-1, IL-2, IL-4, IL-10, or IL-15), an interferon (e.g., IFNγ), a granulocyte macrophage colony stimulating factor (GM-CSF), a tumor necrosis factor (e.g., TNFα), a chemokine (e.g., RANTES, MCP-1, MCP-2, MCP-3, DC-CK1, MIP-1α, MIP-3α, MIP-β, MIP-3β, an α or C—X—C chemokine (e.g., IL-8, SDF-1β, 8DF-1α, GRO, PF-4 and MIP-2). Other chemokines that can be usefully expressed are in the C family of chemokines (e.g., lymphotactin and CX3C family chemokines).

Intercellular adhesion molecules are transmembrane proteins within the immunoglobulin superfamily that act as mediators of adhesion of leukocytes to vascular endothelium and to one another. The vectors described herein can be made to express ICAM-1 (also known as CD54), and/or another cell adhesion molecule that binds to T or B cells (e.g., ICAM-2 and ICAM-3).

Costimulatory factors that can be expressed by the vectors described herein are cell surface molecules, other than an antigen receptor and its ligand, that are required for an efficient lymphocytic response to an antigen (e.g., B7 (also known as CD80) and CD40L).

When used for gene therapy, the transgene encodes a therapeutic transgene product, which can be either a protein or an RNA molecule.

Therapeutic RNA molecules include, without limitation, antisense RNA, inhibitory RNA (RNAi), and an RNA ribozyme. The RNA ribozyme can be either cis or trans acting, either modifying the RNA transcript of the transgene to afford a functional RNA molecule or modifying another nucleic acid molecule. Exemplary RNA molecules include, without limitation, antisense RNA, ribozymes, or RNAi to nucleic acids for huntingtin, alpha synuclein, scatter factor, amyloid precursor protein, p53, VEGF, etc.

Therapeutic proteins include, without limitation, receptors, signaling molecules, transcription factors, growth factors, apoptosis inhibitors, apoptosis promoters, DNA replication factors, enzymes, structural proteins, neural proteins, and histone or non-histone proteins. Exemplary protein receptors include, without limitation, all steroid/thyroid family members, nerve growth factor (NGF), brain derived neurotrophic factor (BDNF), neutotrophins 3 and 4/5, glial derived neurotrophic factor (GDNF), cilary neurotrophic factor (CNTF), persephin, artemin, neurturin, bone morphogenetic factors (B M1's), c-ret, gp 130, dopamine receptors (D 1D5), muscarinic and nicotinic cholinergic receptors, epidermal growth factor (EGF), insulin and insulin-like growth factors, leptin, resistin, and orexin. Exemplary protein signaling molecules include, without limitation, all of the above-listed receptors plus MAPKs, ras, rac, ERKs, NFKβ, GSK3β, AKT, and PI3K. Exemplary protein transcription factors include, without limitation, ~300, CBP, HIF-1alpha, NPAS1 and 2, HIF-1β, p53, p73, nurr 1, nurr 77, MASHs, REST, and NCORs. Exemplary neural proteins include, without limitation, neurofilaments, GAP-43, SCG-10, etc. Exemplary enzymes include, without limitation, TH, DBH, aromatic amino acid decarboxylase, parkin, unbiquitin E3 ligases, ubiquitin conjugating enzymes, cholineacetyltransferase, neuropeptide processing enzymes, dopamine, VMAT and other catecholamine transporters. Exemplary histones include, without limitation, H1-5. Exemplary non-histones include, without limitation, ND10 proteins, PML, and HMG proteins. Exemplary pro- and anti-apoptotic proteins include, without limitation, bax, bid, bak, bc1-xs, bc1-x1, bc1-2, caspases, SMACs, and IAPs.

The one or more vectors individually or collectively encoding all essential HSV genes but excluding all cleavage/packaging signals can either be in the form of a set of vectors or a single bacterial-artificial chromosome ("BAC"), which is formed, for example, by combining the set of vectors to create a single, doublestranded vector. Preparation and use of a five cosmid set is disclosed in (Fraefel et al., "Helper virus-free transfer of herpes simplex virus type 1 plasmid vectors into neural cells," *J. Virol.*, 70:7190-7197, 1996). Ligation of the cosmids together to form a single BAC is disclosed in Stavropoulos and Strathdee (*J. Virol.* 72:7137-43, 1998). The BAC described in Stavropoulos and Strathdee includes a pac cassette inserted at a BamHI site located within the UL41 coding sequence, thereby disrupting expression of the HSV-1 virion host shutoff protein.

By "essential HSV genes", it is intended that the one or more vectors include all genes that encode polypeptides that are necessary for replication of the amplicon vector and structural assembly of the amplicon particles. Thus, in the absence of such genes, the amplicon vector is not properly replicated and packaged within a capsid to form an amplicon particle capable of adsorption. Such "essential HSV genes" have previously been reported in review articles by Roizrnan (*Proc. Natl. Acad. Sci. USA* 11:307-1 13, 1996; *Acta Viroloeica* 43:75-80, 1999. Another source for identifying such essential genes is available at the Internet site operated by the Los Alamos National Laboratory, Bioscience Division, which reports the entire HSV-1 genome and includes a table identifying the essential HSV-1 genes. The genes currently identified as essential are listed in the Table provided as FIG. 10.

Formulation and Administration of hf-HSV amplicon Particles

The hf-HSV amplicon particles described herein can be administered to patients directly or indirectly; alone or in combination with other therapeutic agents; and by any route of administration. For example, the hf-HSV amplicon particles can be administered to a patient indirectly by administering cells transduced with the vector to the patient. Alternatively, or in addition, an hf-HSV amplicon particle could be administered directly. For example, an hf-HSV amplicon particle that expresses an immunostimulatory protein or a tumor-specific antigen can be introduced into a tumor by, for example, injecting the vector into the tumor or into the vicinity of the tumor (or, in the event the cancer is a blood-bourne tumor, into the bloodstream).

Administration of HSV-immunomodulatory protein amplicons encoding cytokines such as IL-2, GM-CSF and RANTES, intercellular adhesion molecules such as ICAM-1 and costimulatory factors such as B7.1 all provide therapeutic benefit in the form of reduction of preexisting tumor size, a vaccine-effect protecting against tumor growth after a subsequent challenge, or both (see U.S. Pat. No. 6,051,428; see also Kutubuddin et al., *Blood* 93:643-654, 1999). The helper virus-free HSV vectors disclosed herein can be administered in the same manner.

The herpesvirus amplicon particles described herein, and cells that contain them, can be administered, directly or indirectly, with other species of HSV-transduced cells (e.g., HSV-immunomodulatory transduced cells) or in combination with other therapies, such as cytokine therapy. Such administrations may be concurrent or they may be done sequentially. Thus, in one embodiment, HSV amplicon particles, the vectors with which they are made (i.e., packaging vectors, amplicon plasmids, and vectors that express an accessory protein) can be injected into a living organism or patient (e.g., a human patient) to treat, for example, cancer or an infectious disease. In further embodiments, one or more of these entities can be administered after administration of a therapeutically effective amount of a cytokine.

EXAMPLES

Example 1

HSV Amplicon Vector-Mediated Transduction of Murine Dendritic Cells

We have constructed amplicon particles that encode the model tumor antigen ovalbumin (HSV-OVA) and human prostate-specific antigen (HSV-PSA), a protein that is expressed specifically in prostate epithelium and prostate carcinoma cells.

As shown in FIG. 1, dendritic cells can be transduced with HSV amplicons. Murine dendritic cells were infected overnight with HSV-creGFP or, as a negative control, a comparable vector that did not include a fluorescent marker (HSV-OVA). The cells were viewed under a microscope (without fixation) with phase contrast optics and with fluorescent light appropriate for visualizing GFP. The cells, as they appeared by phase contrast following transduction with the HSV-creGFP amplicon and the HSV-OVA amplicion, are shown in the upper and lower left-hand panels of FIG. 1, respectively. When viewed with fluorescent light, the cells successfully transduced with the HSV-creGFP amplicon fluoresce (upper right-hand panel of FIG. 1), but none of the HSV-OVA-transduced cells do (lower right-hand panel of FIG. 1).

Example 2

Dendritic Cells Transduced with HSV Amplicons Present Antigen to T Cell Hybridomas As in Example 1, murine dendritic cells (obtained from a C57B1/6×BALB/cByJ)F1 mouse) were infected with an HSV-OVA amplicon and, as a negative control, a comparable population of dendritic cells were infected with an HSV-PSA amplicon. The dendritic cells were then cultured overnight with CTL hybridoma B3Z cells that (1) have been transfected with a construct in which the lacZ gene, encoding β-galactosidase, is placed under the control of an IL-2 promoter (NFAT) and (2) become activated in the presence of ovalbumin. (We have also developed class I-restricted CTL hybridomas specific for PSA). The construct is illustrated at the top of FIG. 2. Following T cell activation, the NFAT promoter is bound, the lacZ gene is transcribed, and the cells in which β-galactosidase is produced turn blue upon staining with X-gal (a standard assay). The hybridoma cells, as they appear following X-gal staining, are shown in the lower half of FIG. 2. No T cells co-cultured with HSV-PSA-transfected dendritic cells turned blue (left-hand photograph), but many of those co-cultured with HSV-OVA-transfected cells did (right-hand panel). The fact that T cells were activated means that the dendritic cells were not only successfully transduced, but also processed OVA for class I MHC presentation.

Infection of DCs with HSV-PSA and co-culture with CTL hybridomas specific for PSA can be used to evaluate presentation of PSA. In fact, infection with an HSV-based amplicon that expresses any antigen of interest can be similarly tested for presentation.

Example 3

Mice Immunized with HSV Amplicon-Transduced Dendritic Cells Respond by Producing Antigen-Specific Cytotoxic T Lymphocytes Dendritic cells were infected in cell culture with one of two amplicons: an HSV-PSA amplicon or an HSV-OVA amplicon, each at an MOI of 1. The transduced cells were used to immunize mice (BALB/c mice were immunized with HSV-PSA-transduced dendritic cells and C57B1/6 mice were immunized with HSV-OVA-transduced dendritic cells, as illustrated in FIG. 3). The cells were injected subcutaneously on day 1 and day 7. Splenocytes were subsequently obtained from the immunized animals and placed in cell culture where they were re-stimulated for five days with irradiated, lipopolysaccharide-treated B cells blasts with the immunodominant peptide of PSA or OVA. CTL responses were measured using a standard $^{51}$Cr release assay. The results, which are presented in FIG. 3 as plots of % specific lysis vs. E:T ratio (the ratio of effector cell to target cell), demonstrate that mice immunized with dendritic cells infected with HSV-OVA or HSV-PSA generate specific CTL responses that can be detected in vitro.

Example 4

Dendritic Cells Infected with HSV-p35 Amplicons and Activated with CpG Oligonucleotides Produce Increased Levels of IL-12 p70 Heterodimer We have also used amplicons to express IL-12 in activated DCs to enhance Th1-mediated responses (FIG. 4). IL-12 is a product of activated APCs and is an important activator of NK and T cell responses. Dendritic cells were infected in cell culture with one of two amplicons: an HSV-PSA amplicon (which served as a control) or an HSV-p35 amplicon (p35 is a subunit of IL-12). Following infection, the dendritic cells were activated with oligonucleotides that contain an immunostimulatory sequence (CpG) or with control oligonucleotides in which the CpG sequence is altered to GpC. Supernatants were collected 48 hours later and tested in an IL-12 ELISA specific for IL-12 p70 heterodimer. As shown in FIG. 4, IL-12 p70 expression was almost nil in cells that were infected with either HSV-PSA or HSV-p35 and stimulated with the control oligonucleotides. There was a low level of IL-12 p70 expression when HSV-PSA-infected cells were stimulated with CpG oligonucleotides and robust expression from HSV-p35-infected cells stimulated with CpG oligonucleotides. These experiments demonstrate that, as shown above, dendritic cells can be successfully transduced with HSV-based amplicons and that the antigen encoded by the amplicon can be induced by appropriate stimuli.

Taken together, the studies described above support the use of DCs infected with HSV-1 amplicon particles in investigations of CTL activation and in immunotherapies to treat cancer and other diseases. The studies described herein provide direct evidence that these HSV-based amplicons can effectively infect cells that remain functional in their ability to present antigen, which is crucial to their use as therapeutic agents (e.g., when formulated as vaccines).

Example 5

Fibroblasts Infected with an HSV-gp120 Amplicon Express gp120

Immunotherapeutic agents for the treatment of HIV infection are likely to be more effective if they can induce or enhance CD4$^+$- and CD8$^+$-T cell activity. To develop such agents, we generated an amplicon vector that encodes the HIV envelope glycoprotein (HSVgp120). The construct was packaged using a modified BAC-based expression system, and gp120 expression was initially monitored by Western blot analysis. As described further below, NIH 3T3 cells infected with HSVgp120 produced high levels of the HIV glycoprotein.

NIH 3T3 cells were cultured and infected with an HSV-gp120 amplicon. Lysates were then prepared and the proteins in them were analyzed. More specifically, 20 μg samples of cell lysates were isolated from uninfected NIH 3T3 cells (this sample served as a control) and HSV-gp120-infected NIH 3T3 cells, separated electrophoretically on a 10% SDS-polyacrylamide gel, and transferred to a nylon membrane that was incubated with an HIV gp120-specific antibody (Clontech, Inc.). The gp120-specific bands were visualized on film using chemiluminescent detection. As shown in FIG. 5, uninfected cells expressed virtually no gp120, whereas HSV-gp120-infected cells expressed substantial amounts of this protein. The lanes designated 1 μl and 10 μl in FIG. 5 represent two different volumes of virus stock used to infect the cells. This high level of expression demonstrates that fibroblasts can be readily infected with an HSV amplicon.

Example 6

Animals Immunized with an HSV-gp120 Amplicon Display a Cell-Mediated Immune Response We next tested the ability of the HSV-gp120 vector to elicit gp120-specific immune responses in BALB/c mice. We were able to detect strong responses to a single intramuscular injection, at both the humoral and cellular level. Anti-Env IgG antibodies were generated (see below and FIG. 6). Cellular immune responses were detected in an interferon-gamma Elispot assay using the class I-restricted V3 peptide recognized by the mice (RGPGRAFVT (SEQ ID NO:1); see Example 7 and FIG. 7)). In these experiments, HSV amplicons expressing a modified MN gp120 induced interferon gamma-producing T cells that were equivalent to those induced by live herpesvirus vectors, and that far exceeded those induced by a modified vaccinia Ankara vector.

To determine whether animals immunized with an HSV-gp120 amplicon could later mount a cell-mediated immune response to the gp120 antigen, mice were immunized with either (1) an HSV-gp120 amplicon, (2) a sequence encoding the V3 peptide (MVA.H), or (3) an HSV-lacZ amplicon. "Naïve" mice constituted a fourth group. Following immunization, the mice were sacrificed and their splenocytes were placed in culture. The cellular responses to a class I-restricted peptide from gp120 (RGPGRAFVTI (SEQ ID NO:13)) were measured by interferon gamma Elispot. Splenocytes incubated without the gp120 peptide served as another control for this study. The number of interferon-gamma-positive spots per well was plotted for each animal, in triplicate, with three dilutions of input splenocytes (100,000; 200,000; and 400,000 cells/well). The results are shown in FIG. 6. The designations A1-A4 represent splenocytes obtained from individual animals, and the (+) and (−) symbols beneath those designations mark splenocytes incubated with or without the specific gp120 peptide. As shown in FIG. 6, the number of interferon gamma-positive spots (which is indicative of the ability of the cells to mount a cell-mediated immune response) was low and not significantly different in splenocytes obtained from mice that were immunized with MVA or HSV-lacZ or that were not immunized at all (naïve). However, significantly more of the splenocytes obtained from HSV-gp120-immunized mice produced interferon following exposure to the gp120 peptide in culture.

Example 7

Animals Infected with HSV-gp120 also Exhibit a Humoral Immune Response

Mice were immunized with either an HSV-gp120 amplicon or an HSV-lacZ amplicon (which served as a negative control). Serum was obtained either before the animals were infected or three weeks afterward and analyzed for anti-env IgG antibodies. The results are shown in FIG. 7. The numbers on the y-axis represent individual animals (four were immunized with HSV-gp120 and two were immunized with HSV-lacZ); the astericks above some bars of the graph represent titers detected at the 1:160 final dilution; and the "+" above other bars denotes titers determined at the 1:10 dilution. The anti-env IgG response in serum obtained three weeks after immunization with HSV-gp120 was substantially greater than in serum obtained from the animals prior to immunization or in serum obtained from animals immunized with HSV-lacZ. Thus, humoral as well as cell-mediated immune responses result.

Example 8

HSV-gp120 Induces CTL Activity in Vivo

BALB/c mice (n=3) were inoculated with an HSV-gp120 amplicon ($10^6$ pfu) by intramuscular injection. The mice were sacrificed 21 days later, and splenocytes were harvested and placed in culture, where they were restimulated in the presence of LPS blasts loaded with the HIVgp120 specific peptide RGPRAFVTI (SEQ ID NO:14). After five days, these effector cells were mixed at various ratios with radiolabeled P815 target cells, either pulsed with peptide (+) or unpulsed (−). Cell killing was assessed using the JAM assay method described by Matzinger et al. (*J. Immunol. Methods* 145:185-92, 1991). The data, shown in FIG. 8, were expressed in terms of % cytotoxicity at each effector to target (E:T) ratio. A1, A2, and A3 denote data obtained from individual animals. These data demonstrate that a single intramuscular injection of an HSV-gp120 vector is sufficient to produce a strong, peptide-specific, cytotoxic effector response in the treated animals.

Example 9

Subcutaneous Administration of an HSV-gp120 Amplicon can Produce a Greater Cellular Immune Response than Other Routes of Administration To study the effect of the route of administration on the strength of the immune response generated, BALB/c mice were inoculated with the same vector, an HSV-gp120 amplicon ($10^6$ expressing viral particles) administered either intramuscularly (into the thigh), subcutaneously (at the base of the tail), or intraperiotoneally. Control mice received $10^6$ pfu of the HSV-lacZ vector intramuscularly. All animals were sacrificed 21 days later, and their splenocytes were harvested and subjected to an interferon-gamma Elispot assay using either an HIVgp120 specific peptide (RGPRAFVTI (SEQ ID NO:14); designated "+" in FIG. 9) or no peptide (designated "−" in FIG. 9). A1, A2, and A3 designate splenocytes obtained from individual animals. As shown in FIG. 9, while all routes of administration produced some number of interferon-gamma-positive spots per well, the greatest number were produced when the antigen had been administered subcutaneously. Thus, subcutaneous inoculation with HSV-gp120 produced the best cellular immune response (at least as defined in this assay system under the parameters used).

The experiments described above show that amplicons can infect DCs, which function in vitro and in vivo. Moreover, direct injection of amplicons results in effective immunization in vivo. Thus, these vectors provide a useful platform for a variety of antigens, including HIV antigens, and the HSV amplicon-based vector systems described herein can be used to treat HIV infection.

Example 10

Production of a Helper Virus-Free Amplicon Particle

As noted above, HSV-based amplicon particles are attractive gene delivery tools, and they are particularly well suited for delivering gene products to neurons (e.g. neurons in the central nervous system) because they are easy to manipulate, can carry large transgenes, and are naturally neurotropic (Geller and Breakefield, *Science* 241:1667-1669, 1988; Spaete and Frenkel, *Cell* 30:305-310, 1982; Federoff et al., *Proc. Natl. Acad. Sci. USA* 89:1636-1640, 1992; Federoff *in Cells: A Laboratory Manual*, Spector et al., Eds., Cold Spring Harbor Press, Cold Spring Harbor, N.Y., 1997; Frenkel et al., in *Eucaryotic Viral Vectors*, Gluzman, Ed., Cold Spring Harbor Press, Cold Spring Harbor, N.Y., 1982). Efforts to bring this vector system into the clinical arena to treat neurodegenerative disease have been hampered by potential cytotoxicites that are associated with traditional methods of virus packaging. This problem involves the co-packaging of helper virus that encodes cytotoxic and immunogenic viral proteins. Newer methods of packaging have been developed that result in helper virus-free amplicon stocks (Fraefel et al., *J. Virol.* 70:7190-7197, 1996; Stavropoulos and Strathdee, *J. Virol.* 72:7137-7143, 1998; see also U.S. Pat. Nos. 5,851,826 and 5,998,208). Stocks prepared by these methods, however, are typically low titer (<$10^5$ expression units/ml), allowing for only modest scale experimentation, primarily in vitro. Such low titers make large animal studies difficult, if not impossible. Present helper virus-free packaging strategies lead to not only lower amplicon titers, but also to stocks that exhibit a high frequency of pseudotransduction events when used to infect a variety of cell types.

Optimal propagation of wild-type HSV virions requires orderly progression of $\alpha$, $\beta$, and $\gamma$ gene transcription following infection of a host cell. This is achieved by delivery of co-packaged proteins, carried by the virion, that help co-opt the cell's transcription machinery and transactivation of viral $\alpha$ gene promoters. This information is fundamental to the development of our helper virus-free system. Helper virus-based packaging involves superinfection of an amplicon DNA-transfected monolayer of packaging cells with a replication-defective helper virus. The helper virus genome, as in the case of wild-type HSV, is delivered to the cell in a complex with co-packaged proteins, including VP16 and virion host shutoff (vhs). The HSV vhs protein functions to inhibit the expression of genes in infected cells via destabilization of both viral and host mRNAs. Because vhs plays such a vital role in establishing the HSV replicative cycle and is a potential structural protein, we hypothesized that its presence during amplicon packaging accounted for the higher titers obtained with helper virus-based packaging systems. VP16 is another co-packaged protein that resides in the helper virus nucleocapsid and is responsible for activating transcription of HSV immediate-early genes to initiate the cascade of lytic cycle-related viral protein expression.

In contrast to helper virus-based packaging systems, helper virus-free systems involve co-transfection of naked DNA forms of either an HSV genome-encoding cosmid set or BAC reagent with an amplicon vector (e.g., a plasmid). Thus, the HSV genome gains access to the cell without co-packaged vhs or VP16. The initiation and temporal progression of HSV gene expression is, we speculated, not optimal for production of packaged amplicon vectors due to the absence of these important HSV proteins. To test our hypothesis—that the efficiency of amplicon packaging would be increased by introducing vhs and/or VP16 during the initial phase of virus propagation—we included a vhs-encoding DNA segment in the packaging protocol as a co-transfection reagent. In some instances, packaging cells were "pre-loaded" with VP16 to mimic its presence during helper virus-mediated amplicon packaging. As shown below, these modifications led to a 30- to 50-fold enhancement of packaged amplicon vector titers, nearly approximatig titers obtained using helper virus-based traditional approaches. In addition, the viral stocks failed to exhibit the pseudotransduction phenomenon. These improvements make large-scale in vivo applications much more likely. The methods used to make a helper virus-free amplicon particles are described first, followed by a description of the results obtained.

Cell culture: Baby hamster kidney (BHK) cells were maintained as described by Lu et al. (*Human Gene Ther.* 6:421-430, 1995). NIH 3T3 cells were originally obtained from the American Type Culture Collection and were maintained in Dulbecco's modified Eagle medium (DMED) supplemented with 10% fetal bovine serum, penicillin, and streptomycin.

Plasmid construction: The HSVPrPUC/CMVegfp amplicon plasmid was constructed by cloning the 0.8-kb cytomegalovirus (CMV) immediate early promoter and 0.7-kb enhanced gree fluorescent protein cDNA (Clontech, Inc.) into the BamHI restriction enzyme site of the pHSVPrPUC amplicon vector (Geller et al., *Proc. Natl. Acad. Sci. USA* 87:8950-8954, 1990). A 3.5 kb HpaI/HindIII fragment encompassing the UL41 (vhs) open reading frame and its 5' and 3' transcriptional regulatory elements was removed from cos 56 (Cunningham and Davison, *Virol.* 197:116-124, 1993) and cloned into pBSKSII (Stratagene, Inc.) to create pBSKS(vhs). For construction of pGRE$_5$vp16, the VP16 coding sequence was amplified by PCR from pBAC-V2 using gene-specific oligonucleotides that possess EcoRI(5'-CGGAATTCCGCAG-GTTTTGTAATGTATGTGCTCGT-3' (SEQ ID NO:2) and HindIII (5'-CTCCGAAGCTTAAGC-CCGATATCGTCTTTCCCGTATCA-3' (SEQ ID NO:3)) restriction enzyme sequences that facilitate cloning into the pGRE$_5$-2 vector (Mader and White, *Proc. Natl. Acad. Sci. USA* 90:5603-5607, 1993).

Helper virus-free Amplicon Packaging: On the day prior to transfection, $2 \times 10^6$ BHK cells were seeded on a 60-mm culture dish and incubated overnight at 37° C. The following procedures were followed for cosmid-based packaging. The day of transfection, 250 μl Opti-MEM (Gibco-BRL, Bethesda, Md.), 0.4 μg of each of five cosmid DNAs (kindly provided by Dr. A. Geller, and 0.5 μg amplicon vector DNA, with or without varying amounts of pBSKS(vhs) plasmid DNA were combined in a sterile polypropylene tube (Fraefel et al., *J. Virol.* 70:7190-7197, 1996). The following procedures were followed for BAC-based packaging. 250 μl Opti-MEM (Gibco-BRL, Bethesda, Md.), 3.5 μg of pBAC-V2 DNA (kindly provided by Dr. C. Strathdee, and 0.5 μg amplicon vector DNA, with or without varying amounts of pBSKS (vhs) plasmid DNA were combined in a sterile polypropylene tube (Stavropoulos and Strathdee, *J. Virol.* 72:7137-7143, 1998). The protocol for both cosmid- and BAC-based packaging was identical from the following step forward. Ten microliters of Lipofectamine Plus™ reagent (Gibco-BRL) were added over a 30-second period to the DNA mix and allowed to incubate at room temperature for 20 minutes. In a separate tube, 15 µl Lipofectamine (Gibco-BRL) were mixed with 250 µl Opti-MEM. Follwing the 20 minute incubation, the contents of the two tubes were combined over a one-minute period and then incubated for an additional 20 minutes at room temperature. During the second incubation, the medium in the seeded 60 mm dish was removed and replaced with 2 ml Opti-MEM. The transfection mix was added to the flask and allowed to incubate at 37° C. for five hours. The transfection mix was then diluted with an equal volume of DMEM plus 20% FBS, 2% penicillin/streptomycin, and 2 mM hexamethylene bis-acetamide (HMBA), and incubated overnight at 34° C. The following day, medium was removed and replaced with DMEM plus 10% FBS, 1% penicillin/streptomycin, and 2 mM HMBA. The packaging flask was incubated an additional three days and virus was harvested and stored at −80° C. until purification. Viral preparations were subsequently thawed, sonicated, and clarified by centrifugation (3000×g for 20 minutes). Viral samples were stored at −80° C. until use.

For concentrated viral stocks, viral preparations were subsequently thawed, sonicated, clarified by centrifugation, and concentrated by ultracentrifugation through a 30% sucrose cushion (Geschwind et al., Providing pharmacological access to the brain in *Methods in Neuroscience*, Conn, Ed., Academic Press, Orlando, Fla., 1994). Viral pellets were resuspended in 100 µl PBS and stored at −80° C. until use. For packaging experiments examining the effect of VP16 on amplicon titers, the cells plated for packaging were first allowed to adhere to the 60 mm culture dish for 5 hours and subsequently transfected with pGRE$_5$vp16 using the Lipofectamine reagent as described above. Following a five-hour incubation, the transfection mix was removed, complete medium (DMEM plus 10% FBS, 1% penicillin/streptomycin) was added, and the cultures were incubated at 37° C. until the packaging co-transfection step the next day.

Viral titering: Amplicon titers were determined by counting the number of cells expressing enhanced green fluorescent protein (HSVPrPUC/CMVegfp amplicon) or β-galactosidase (HSVlac amplicon). Briefly, 10 µl of concentrated amplicon stock was incubated with confluent monolayers ($2 \times 10^5$ expressing particles) of NIH 3T3 cells plated on glass coverslips. Following a 48-hr incubation, cells were either fixed with 4% paraformaldehyde for 15 min at RT and mounted in Mowiol for fluorescence microscopy (eGFP visualization), or fixed with 1% glutaraldehyde and processed for X-gal histochemistry to detect the lacZ transgene product. Fluorescent or X-gal-stained cells were enumerated, expression titer calculated, and represented as either green-forming units per ml (gfu/ml) or blue-forming units per ml (bfu/ml), respectively.

TaqMan Quantitative PCR System: To isolate total DNA for quantitation of amplicon genomes in packaged stocks, virions were lysed in 100-mM potassium phosphate pH 7.8 and 0.2% Triton X-100. Two micrograms of genomic carrier DNA was added to each sample. An equal volume of 2× Digestion Buffer (0.2 M NaCl, 20 mM Tris-Cl pH 8.0, 50 mM EDTA, 0:5% SDS, 0.2 mg/ml proteinase K) was added to the lysate and the sample was incubated at 56° C. for 4 hrs. Samples were processed further by one phenol:chloroform, one chloroform extraction, and a final ethanol precipitation. Total DNA was quantitated and 50 ng of DNA was analyzed in a PE7700 quantitative PCR reaction using a designed lacZ-specific primer/probe combination multiplexed with an 18S rRNA-specific primer/probe set. The lacZ probe sequence was 5'-6FAM-ACCCCGTACGTCTTCCCGAGCG-TAMRA-3' (SEQ ID NO:4); the lacZ sense primer sequence was 5'-GGGATCTGCCATTGTCAGACAT-3' (SEQ ID NO:5); and the lacZ antisense primer sequence was 5'-TG-GTGTGGGCCATAATTCAA-3' (SEQ ID NO: 12). The 18S rRNA probe sequence was 5'-JOE-TGCTGGCACCAGACT-TGCCCTC-TAMRA-3' (SEQ ID NO:6); the 18S sense primer sequence was 5'-CGGCTACCACATCCAAGGAA-3' (SEQ ID NO:7); and the 18S antisense primer sequence was 5'-GCTGGAATTACCGCGGCT-3' (SEQ ID NO:8).

Each 25-µl PCR sample contained 2.5 µl (50 ng) of purified DNA, 900 nM of each primer, 50 nM of each probe, and 12.5 µl of 2× Perkin-Elmer Master Mix. Following a 2-min 50° C. incubation and 2-min 95° C. denaturation step, the samples were subjected to 40 cycles of 95° C. for 15 sec. and 60° C. for 1 min. Fluorescent intensity of each sample was detected automatically during the cycles by the Perkin-Elmer Applied Biosystem Sequence Detector 7700 machine. Each PCR run included the following: no-template control samples, positive control samples consisting of either amplicon DNA (for lacZ) or cellular genomic DNA (for 18S rRNA), and standard curve dilution series (for lacZ and 18S). Following the PCR run, "real-time" data were analyzed using Perkin-Elmer Sequence Detector Software version 1.6.3 and the standard curves. Precise quantities of starting template were determined for each titering sample and results were expressed as numbers of vector genomes per ml of original viral stock.

Western blot analysis: BHK cell monolayers ($2 \times 10^6$ cells) transfected with varying packaging components were lysed with RIPA buffer (150 mM NaCl, 1% NP-40, 0.5% DOC, 0.5% SDS, and 50 mM Tris-Cl, pH 8). Equal amounts of protein were electrophoretically separated on a 10% SDS-PAGE gel and transferred to a PVDF membrane. The resultant blot was incubated with an anti-VP16 monoclonal antibody (Chemicon, Inc.), and specific VP16 immunoreactive band visualized using an alkaline phosphatase-based chemiluminescent detection kit (ECL).

Cytotoxicity Assays: The effect of BAC-packaged HSVlac stocks prepared in the presence or absence of VP16 and/or vhs on cell viability was determined using a lactate dehydrogenase (LDH) release-based assay (Promega Corp., Madison, Wis.). Equivalent expression units of virus from each packaging sample were used to transduce $5 \times 10^3$ NIH 3T3 cells in 96-well flat-bottomed culture dishes. Quantitation of LDH release was performed according to manufacturer's instructions. Viability data were represented as normalized cell viability index.

Stereotactic injections: Mice were anesthetized with Avertin at a dose of 0.6 ml per 25 g body weight. After positioning in an ASI murine stereotactic apparatus, the skull was exposed via a midline incision, and burr holes were drilled over the following coordinates (bregma, +0.5 mm; lateral −2.0 mm; and deep, −3.0 mm) to target infections to the striatum. A 33 GA steel needle was gradually advanced to the desired depth, and 3 µl (equivalent in vitro titer) HSVPrPUC/CMVegfp virus was infused via a microprocessor-controlled pump over 10 minutes (UltraMicroPump, World Precision Instruments, Sarasota Springs, Fla.). The injector unit was mounted on a precision small animal stereotaxic frame (ASI Instruments, Warren, Mich.) micromanipulator at a 90° angle using a mount for the injector. Viral injections were performed at a constant rate of 300 nl/min. The needle was removed slowly over an additional 10-minute period.

Tissue preparation and GFP VISUALIZATION: Infected mice were anesthetized four days later, a catheter was placed into the left ventricle, and intracardiac perfusion was initiated with 10 ml of heparinized saline (5,000 U/L saline) followed by 60 ml of chilled 4% PFA. Brains were extracted and postfixed for 1-2 hours in 4% PFA at 4° C. Subsequently, brains were cryoprotected in a series of sucrose solutions with a final solution consisting of a 30% sucrose concentration (w/v) in PBS. Forty micron serial sections were cut on a sliding microtome (Micron/Zeiss, Thornwood, N.Y.) and stored in a cryoprotective solution (30% sucrose (w/v), 30% ethylene glycol in 0.1 M phosphate buffer (pH 7.2)) at −20° C. until processed for GFP visualization. Sections were placed into Costar net wells (VWR, Springfield, N.J.) and incubated for 2 hrs in 0.1 M Tris buffered saline (TBS) (pH 7.6). Upon removal of cryoprotectant, two additional 10 min washes in 0.1 M TBS with 0.25% Triton X-100 (Sigma, St. Louis, Mo.) were performed. Sections were mounted with a fine paint brush onto subbed slides, allowed to air dry, and mounted with an aqueous mounting media, Mowiol. GFP-positive cells were visualized with a fluorescent microscope (Axioskop, Zeiss, Thornwood, N.Y.) utilizing a FITC cube (Chroma Filters, Brattleboro, Vt.). All images used for morphological analyses were digitally acquired with a 3-chip color CCD camera at 200× magnification (DXC-9000, Sony, Montvale, N.J.).

Morphological analyses: Cell counts were performed on digital images acquired within 24 hrs of mounting. At the time of tissue processing coronal slices were stored serially in three separate compartments. All compartments were processed for cell counting and GFP(+) cell numbers reflect cell counts throughout the entire injection site. All spatial measurements were acquired using an image analysis program (Image-Pro Plus, Silver Spring, Md.) at a final magnification of 200×. Every section was analyzed using identical parameters in three different planes of focus throughout the section to prevent repeated scoring of GFP(+) cells. Each field was analyzed by a computer macro to count cells based on the following criteria: object area, image intensity (fluorescent signal) and plane of focus. Only cells in which the cell body was unequivocally GFP(+) and nucleus clearly defined were counted. Every section that contained a GFP(+) cell was counted. In addition, a watershed separation technique was applied to every plane of focus in each field to delineate overlapping cell bodies. The watershed method is an algorithm that is designed to erode objects until they disappear, then dilates them again such that they do not touch.

Statistical Analyses: Statistical analyses were carried out using one-way analyses of variance (ANOVA) with plasmid construct as the between-group variable. Two-way repeated measure analyses of variance (RMANOVA) were carried out using plasmid construct as the between-group variable and time interval as a within-group variable.

Results: Prior to the methods described herein, widespread use of helper virus-free HSV particles has been hampered by helper virus-mediated cytotoxicity associated with traditionally packaged amplicon stocks or by the low titers obtained from helper virus-free production methods. Helper virus-free methods of packaging hold the most promise as resultant stocks exhibit little or no cytotoxicity. As shown here, modifications to such packaging strategies could be made to increase viral titers.

We utilized both cosmid- and BAC-based methods of helper virus-free packaging previously described (Fraefel et al., *J Virol* 70:719-7197, 1996; Stavropoulos and Strathdee, *J. Virol.* 72:7137-7143, 1998; and Saeki et al., *Hum. Gene Ther.* 9:2787-2794, 1998). The low titers observed for helper virus-free methods may be a result of the sub-optimal state of the HSV genome at the beginning of amplicon production, as the genome is without co-packaged viral regulators vhs and VP16. To determine if introduction of vhs into the packaging scheme could increase amplicon titers and quality, we cloned a genomic segment of the UL41 gene into pBluescript and added this plasmid (pBSKS(vhs)) to the co-transfection protocols to provide vhs in trans. The genomic copy of UL41 contained the transcriptional regulatory region and flanking cis elements believed to confer native UL41 gene expression during packaging. When pBSKS(vhs) was added to the packaging protocols for production of a β-galactosidase (lacZ)-expressing amplicon (HSVlac), a maximum of 10-fold enhanced amplicon expression titers was observed for both cosmid- and BAC-based strategies. As observed previously, the expression titers for HSVlac virus produced by the BAC-based method were approximately 500- to 1000-fold higher than stocks produced using the modified cosmid set. Even though titers were disparate between the differently prepared stocks, the effect of additionally expressed vhs on amplicon titers was analogous.

The punctate appearance of reporter gene product (pseudotransduction), a phenomenon associated with first-generation helper virus-free stocks, was substantially diminished in vitro when vhs was included in BAC-based packaging of a β-galactosidase-expressing (HSVlac) or an enhanced green fluorescent (GFP)-expressing virus (HSVPrPUC/CMVegfp). Pseudotransduction was not observed, as well, for cosmid-packaged amplicon stocks prepared in the presence of vhs. To assess the ability of the improved amplicon stocks to mediate gene delivery in vivo, BAC-packaged HSVPrPUC/CMVegfp virus prepared in the absence or presence of pBSKS(vhs) was injected stereotactically into the striata of C57BL/6 mice (see above). Four days following infection, animals were sacrificed and analyzed for GFP-positive cells present in the striatum. The numbers of cells transduced by HSVPrPUC/CMVegfp prepared in the presence of vhs were significantly higher than in animals injected with stocks produced in the absence of vhs. In fact, it was difficult to definitively identify GFP-positive cells in animals transduced with vhs(−) amplicon stocks.

The mechanism by which vhs expression resulted in higher apparent amplicon titers in helper virus-free packaging could be attributed to one or several properties of vhs. The UL41 gene product is a component of the viral tegument and could be implicated in structural integrity, and its absence could account for the appearance of punctate gene product material following transduction. For example, the viral particles may be unstable as a consequence of lacking vhs. Thus, physical conditions, such as repeated freeze-thaw cycles or long-term storage, may have led to inactivation or destruction of vhs-lacking virions at a faster rate than those containing vhs.

The stability of HSVPrPUC/CMVegfp packaged via the BAC method in the presence or absence of vhs was analyzed initially with a series of incubations at typically used experimental temperatures. Viral aliquots from prepared stocks of HSVPrPUC/CMVegfp were incubated at 4, 22, or 37° C. for periods up to three hours. Virus recovered at time points 0, 30, 60, 120, and 180 minutes were analyzed for their respective expression titer on NIH 3T3 cells. The rates of decline in viable amplicon particles, as judged by their ability to infect and express GFP, did not differ significantly between the vhs(+) and vhs(−) stocks. Another condition that packaged amplicons encounter during experimental manipulation is freeze-thaw cycling. Repetitive freezing and thawing of virus stocks is known to diminish numbers of viable particles, and potentially the absence of vhs in the tegument of BAC-packaged amplicons leads to sensitivity to freeze fracture. To test this possibility, viral aliquots were exposed to a series of four freeze-thaw cycles. Following each cycle, samples were removed and titered for GFP expression on NIH 3T3 cells as described previously. At the conclusion of the fourth freeze-thaw cycle, the vhs(−) HSVPrPUC/CMVegfp stock exhibited a 10-fold diminution in expression titers as opposed to only a 2-fold decrease for vhs(+) stocks. This observation suggests that not only do vhs(+) stocks have increased expression titers, but the virions are more stable when exposed to temperature extremes, as determined by repetitive freeze-thaw cycling.

The native HSV genome enters the host cell with several viral proteins besides vhs, including the strong transcriptional activator VP16. Once within the cell, VP16 interacts with cellular transcription factors and HSV genome to initiate immediate-early gene transcription. Under helper virus-free conditions, transcriptional initiation of immediate-early gene expression from the HSV genome may not occur optimally, thus leading to lower than expected titers. To address this issue, a VP16 expression construct was introduced into packaging cells prior to cosmid/BAC, amplicon, and pBSKS(vhs) DNAs, and resultant amplicon titers were measured. To achieve regulated expression a glucocorticoid-controlled VP16 expression vector was used (pGRE$_5$vp16).

The pGRE$_5$vp16 vector was introduced into the packaging cells 24 hours prior to transfection of the regular packaging DNAs. HSVlac was packaged in the presence or absence of vhs and/or VP16 and resultant amplicon stocks were assessed for expression titer. Some packaging cultures received 100-nM dexamethasone at the time of pGRE$_5$vp16 transfection to strongly induce VP16 expression; others received no dexamethasone. Introduction of pGRE$_5$vp16 in an uninduced (basal levels) or induced state (100 nM dexamethasone) had no effect on HSVlac titers when vhs was absent from the cosmid- or BAC-based protocol. In the presence of vhs, addition of pGRE$_5$vp16 led to either a two- or five-fold enhancement of expression titers over those of stocks packaged with only vhs (cosmid- and BAC-derived stocks). The effect of "uninduced" pGRE$_5$vp16 on expression titers suggested that VP16 expression was occurring in the absence of dexamethasone. To examine this, Western blot analysis with a VP16-specific monoclonal antibody was performed using lysates prepared from BHK cells transfected with the various packaging components. Cultures transfected with pGRE$_5$vp16/BAC/pBSKS (vhs) in the absence of dexamethasone did show VP16 levels intermediate to cultures transfected either with BAC alone (lowest) or those transfected with pGRE$_5$vp16/BAC/pBSKS (vhs) in the presence of 100 nM dexamethasone (highest). There was no difference in level of pGRE$_5$vp16-mediated expression in the presence or absence of BAC, nor did dexamethasone treatment induce VP16 expression from the BAC.

VP16-mediated enhancement of packaged amplicon expression titers could be due to increased DNA replication and packaging of amplicon genomes. Conversely, the additional VP16 that is expressed via pGRE$_5$vp16 could be incorporated into virions and act by increasing vector-directed expression in transduced cells. To test the possibility that VP16 is acting by increasing replication in the packaging cells, concentrations of vector genomes in BAC-derived vector stocks were determined. HSVlac stocks produced in the presence or absence of vhs and/or VP16 were analyzed using a "real-time" quantitative PCR method. The concentration of vector genome was increased two-fold in stocks prepared in the presence of VP16 and this increase was unaffected by the presence of vhs.

There is a possibility that addition of viral proteins, like vhs and VP16, to the packaging process may lead to vector stocks that are inherently more cytotoxic. The amplicon stocks described above were examined for cytotoxicity using a lactate dehydrogenase (LDH) release-based cell viability assay. Packaged amplicon stocks were used to transduce NIH 3T3 cells and 48 hours following infection, viability of the cell monolayers was assessed by the LDH-release assay. Amplicon stocks produced in the presence of vhs and VP16 displayed less cytotoxicity on a per virion basis than stocks packaged using the previously published BAC-based protocol (Stavropoulos and Strathdee, supra).

Significance: Wild-type HSV virions contain multiple regulatory proteins that prepare an infected host cell for virus propagation. These virally encoded regulators, which are localized to the tegument and nucleocapsid, include vhs and VP16, respectively. The UL41 gene-encoded vhs protein exhibits an essential endoribonucleolytic cleavage activity during lytic growth that destabilizes both cellular and viral mRNA species (Smibert et al., *J. Gen. Virol.* 73:467-470, 1992). Vhs-mediated ribonucleolytic activity appears to prefer the 5' ends of mRNAs over 3' termini, and the activity is specific for mRNA, as vhs does not act upon ribosomal RNAs (Karr and Read, *Virology* 264:195-204, 1999). Vhs also serves a structural role in virus particle maturation as a component of the tegument. HSV isolates that possess disruptions in UL41 demonstrate abnormal regulation of IE gene transcription and significantly lower titers than wild-type HSV-1 (Read and frenkel, *J. Virol.* 46:498-512, 1983), presumably due to the absence of vhs activity. Therefore, because vhs is essential for efficient production of viable wild-type HSV particles, it likely plays a similarly important role in packaging of HSV-1-derived amplicon vectors.

The term "pseudotransduction" refers to virion expression-independent transfer of biologically active vector-encoded gene product to target cells (Liu et al., *J. Virol.* 70:2497-2502, 1996; Alexander et al. *Human Gene Ther.* 8:1911-1920, 1997. This phenomenon was originally described with retrovirus and adeno-associated virus vector stocks and was shown to result in an overestimation of gene transfer efficiencies. β-galactosidase and alkaline phosphatase are two commonly expressed reporter proteins that have been implicated in pseudotransduction, presumably due to their relatively high enzymatic stability and sensitivity of their respective detection assays (Alexander et al., supra). Stocks of β-galactosidase expressing HSVlac and GFP-expressing HSVPrPUC/CMVegfp exhibited high levels of pseudotransduction when packaged in the absence of vhs. Upon addition of vhs to the previously described helper virus-free packaging protocols, a 10-fold increase in expression titers and concomitant decrease in pseudotransduction were observed in vitro.

Vhs-mediated enhancement of HSV amplicon packaging was even more evident when stocks were examined in vivo. GFP-expressing cells in animals transduced with vhs(+) stocks were several hundred-fold greater in number than in animals receiving vhs(−) stocks. This could have been due to differences in virion stability, where decreased particle stability could have led to release of co-packaged reporter gene product observed in the case of vhs(−) stocks. Additionally, the absence of vhs may have resulted in packaging of reporter gene product into particles that consist of only tegument and envelope (Rixon et al., *J. Gen. Virol.* 73:277-284, 1992). Release of co-packaged reporter gene product in either case could potentially activate a vigorous immune response in the CNS, resulting in much lower than expected numbers of vector-expressing cells.

Pre-loading of packaging cells with low levels of the potent HSV transcriptional activator VP16 led to a 2- to 5-fold additional increase in amplicon expression titers only in the presence of vhs for cosmid- and BAC-based packaging systems, respectively. This observation indicates the transactivation and structural functions of VP16 were not sufficient to increase viable viral particle production when vhs was absent, and most likely led to generation of incomplete virions containing amplicon genomes as detected by quantitative PCR. When vhs was present for viral assembly, however, VP16-mediated enhancement of genome replication led to higher numbers of viable particles formed. Quantitative PCR analysis of amplicon stocks produced in the presence of VP16 and vhs showed that viral genomes were increased only 2-fold while expression titers were increased 5-fold over stocks produced in the presence of vhs only. This result suggests that a portion of the effect related to VP16-mediated enhancement of genome replication while the additional ~2-fold enhancement in expression titers may be attributed to the structural role of VP16. The effect of VP16 on expression titers was not specific to amplicons possessing the immediate-early 4/5promoter of HSV, as amplicons with other promoters were packaged to similar titers in the presence of VP16 and vhs.

VP16 is a strong transactivator protein and structural component of the HSV virion (Post et al., Cell 24:555-565, 1981). VP16-mediated transcriptional activation occurs via interaction of VP16 and two cellular factors, Oct-1 (O'Hare and Goding, Cell 52:435-445, 1988; Preston et al, Cell 52:425-434, 1988; Stern et al., Nature 341:624-630, 1989) and HCF (wilson et al., Cell 74:115-125, 1993; Xiao and Capone, Mol. Cell Biol. 10:4974-4977, 1990) and subsequent binding of the complex to TAATGARAT (SEQ IN NO: 16) elements found within HSV IE promoter regions (O'Hare, Semin. Virol. 4:145-155, 1993. This interaction results in robust up-regulation of IE gene expression. Neuronal splice-variants of the related Oct-2 transcription factor have been shown to block IE gene activation via binding to TAATGARAT (SEQ ID NO:16) elements (Lillycrop et al., Neuron 7:381-390, 1991) suggesting that cellular transcription factors may also play a role in limiting HSV lytic growth.

The levels of VP16 appear to be important in determining its effect on expression titers. Low, basal levels of VP16 (via uninduced pGRE$_5$vp16) present in the packaging cell prior to introduction of the packaging components induced the largest effect on amplicon expression titers. Conversely, higher expression of VP16 (via dexamethasone-induced pGRE$_5$vp16) did not enhance virus production to the same degree and may have, in fact, abrogated the process. The presence of glucocorticoids in the serum components of growth medium is the most likely reason for this low-level VP16 expression, as charcoal-stripped sera significantly reduces basal expression from this construct. Perhaps only a low level or short burst of VP16 is required to initiate IE gene transcription, but excessive VP16 leads to disruption of the temporal progression through the HSV lytic cycle, possibly via inhibition of vhs activity. Moreover, evidence has arisen to suggest vhs activity is downregulated by interaction with newly synthesized VP16 during the HSV lytic cycle, thereby allowing for accumulation of viral mRNAs after host transcripts have been degraded (Schmelter et al., J. Virol. 70:2124-2131, 1996; Smibert et al., J. Virol. 68:2333-2346, 1994; Lam et al., EMBO J. 15:2575-2581, 1996). Therefore, a delicate regulatory protein balance may be required to attain optimal infectious particle propagation. Additionally, the 100-nM dexamethasone treatment used to induce VP16 expression may have a deleterious effect on cellular gene activity and/or interfere with replication of the OriS-containing amplicon genome in packaging cells. High levels of dexamethasone have been shown previously to repress HSV-1 OriS-dependent replication by an unknown mechanism Hardwicke and Schaffer, J. Virol. 71:3580-3587, 1997). Inhibition of OriS-dependent replication does not appear to be responsible for our results, however, since quantitative PCR analysis of amplicon stocks produced in the presence and absence of dexamethasone indicated no change in genome content as a function of drug concentration. It is interesting to note that amplicon stocks were prepared in the presence of hexamethylene bisacetamide (HMBA). HMBA has been shown to compensate for the absence of VP16, thus leading to the transactivation of immediate early gene promoters (McFarlane et al., J. Gen. Virol. 73:285-292, 1992. In the absence of HMBA pre-loading a packaging cell with VP16 could impart an even more dramatic effect on titers.

Ectopic expression of vhs and VP16 did not lead to amplicon stocks that exhibited higher cytotoxicity than helper virus-free stocks prepared in the traditional manner when examined by an LDH-release assay. Stocks prepared by the various methods were equilibrated to identical expression titers prior to exposure to cells. The heightened cytotoxicity in stocks produced in the absence of vhs and/or VP16 may reflect that larger volumes of these stocks were required to obtain similar expression titers as the vhs/VP16-containing samples or the levels of defective particles in the former may be significantly higher. Contaminating cellular proteins that co-purify with the amplicon particles are most likely higher in concentration in the traditional stocks, and probably impart the higher toxicity profiles observed.

Example 11

Herpesvirus Amplicon Particles in the Treatment of Hematologic Malignancies

The experiments described below were designed to test viral-based amplicons as therapeutic agents for hematologic (and other types of) malignancies. We transduced tumor cells ex vivo with various HSV-based amplicons that encode different co-stimulatory molecules, such as B7.1 (also known as CD80) and CD40L (also known as CD154). In addition, we tested two HSV amplicon stocks: one packaged using a helper virus (manufactured via a replication-defective helper virus deleted in HSV ICP4) and one prepared, helper virus-free, using a bacterial artificial chromosome (BAC). Stocks packaged in either way were prepared to express either B7.1 or CD40L. The helper virus-containing and the helper virus-free stock were tested for their ability to transduce freshly isolated human B cell chronic lymphocytic leukemia (CLL) cells, to function as antigen-presenting cells, to stimulate T cell proliferative responses and cytokine release, and to affect MHC-I expression in transduced target CLL cells.

Using CLL cells, we found that: (1) both helper virus-containing and helper virus-free virus stocks are able to transduce primary human leukemia cells at high efficiencies, and (2) cells transduced with helper virus-containing amplicon were less efficient as APCs, and thus not as desirable as helper virus-free preparations for use in immunotherapies. The disadvantages of using a helper virus-containing preparation arise from the transcription of certain genes within the HSV genome, which is delivered largely intact into the host cell with the helper virus. More specifically, we found:

(1) loss of MHC-I on cells transduced with helper virus-containing HSV amplicon stocks (this is likely to be mediated by the ICP-47 gene product that is introduced with the helper virus) and (2) increased cytotoxicity in cells transduced by the helper virus-containing amplicon stock. With respect to (1), loss of MHC-I hampers CD8-mediated CTL activity and results in a loss of the ability to kill target tumor cells. With respect to (2), the increased cytotoxicity in CLL cells is most likely related to the introduction of pro-apoptotic genes mediated by the helper virus. Due to these issues (inherent immunosuppression and cytotoxicity), helper virus-free amplicon preparations emerge as a superior choice for developing immunotherapies to treat any number of infectious diseases and cancers (including chronic lymphocytic leukemia).

Cell culture: Samples of blood (10 ml each) were obtained from eight patients with an established diagnosis of CLL. Peripheral blood lymphocytes (PBL) were isolated by density gradient centrifugation on Ficoll-Paque™ Plus (Amersham Pharmacia Biotech AB, Uppsala, Sweden). More than 97% of purified PBL stained positive for CD19 by flow-cytometry. Allogeneic T cells were purified from healthy donor PBL through a T cell enrichment column (R&D Systems, Minneapolis, Minn.). More than 97% of the purified lymphocytes obtained from the T cell column were CD3 positive by flow cytometry. Both CLL cells and T cells were maintained in RPMI supplemented with 10% human AB serum. Baby hamster kidney (BHK) and RR1 cell lines were maintained as described in Kutubuddin et al. (*Blood* 93:643-654, 1999). The NIH 3T3 mouse fibroblast cell line was originally obtained from the American Type Culture Collection (Manassas, Va.) and maintained in Dulbecco's modified Eagle medium (DMEM) plus 10% fetal bovine serum (FBS).

Amplicon Construction: Coding sequences for *E. coli* β-galactosidase and human B7.1 (CD80) were cloned into the polylinker region of the pHSVPrPUC plasmid (Geller et al., *Proc. Natl. Acad. Sci. USA* 87:8950-8954, 1990) as described by Kutubuddin et al. (*Blood* 93643-654, 1999). Murine CD40L (CD154; kindly provided by Dr. Mark Gilber, Immunex Corp.) was cloned into the BamHI and EcoRI sites of the pHSVPrPUC amplicon vector.

Helper virus-based amplicon packaging: Amplicon DNA was packaged into HSV-1 particles by transfecting 5 µg of plasmid DNA into RR1 cells with Lipofectamine as recommended by the manufacturer (GIBCO-BRL). Following incubation for 24 hours, the transfected monolayer was superinfected with the HSV strain 17-derived IE3 deletion mutant virus D30EBA (Paterson and Everett, *J. Gen. Virol.* 71:1775-1783, 1990) at a multiplicity of infection (MOI) of 0.2. Once cytopathic changes were observed in the infected monolayer, the cells were harvested, freeze-thawed, and sonicated using a cup sonicator (Misonix, Inc.). Viral supernatants were clarified by centrifugation at 5000×g for ten minutes prior to repeat passage on RR1 cells. This second viral passage was harvested as above and concentrated for two hours by ultracentrifugation on a 30% sucrose cushion as described by Federoff (*In Cells: A Laboratory Manual*, Spector and Leinwand, Eds., Cold Spring Harbor Laboratory Press, Cold Spring Harbor, N.Y., 1997). Viral pellets were resuspended in PBS ($Ca^{2+}$ and $Mg^{2+}$ free) and stored at −80° C. for future use.

Helper virus-free amplicon packaging (HF-HSV): Amplicon stocks were also prepared using a modified helper virus-free packaging method. The packaging ystem utilizes a bacterial artificial chromosom (BAC; kindly provided by C. Strathdee) that contains the HSV genome without its cognate pac signals as a co-transfection reagent with amplicon DNA. Because the amplicon vector possesses pac signals, only the amplicon genome is packaged. Briefly, on the day prior to transfection, $2\times10^7$ BHK cells were seeded in a T-150 flask and incubated overnight at 37° C. The day of transfection, 1.8 ml Opti-MEM (Gibco-BRL, Bethesda, Md.), 25 µg of pBAC-V2 DNA (Stavropoulos and Strathdee, supra), 7 µg of pBS (vhs), and 3.6 µg amplicon vector DNA were combined in a sterile polypropylene tube. Seventy microliters of Lipofectamine Plus reagent (Gibco-BRL) were added over a period of 30 seconds to the DNA mix and allowed to incubate at 22° C. for 20 minutes. In a separate tube, 100 µl Lipofectamine (Gibco-BRL) was mixed with 1.8 ml Optim-MEM and also incubated at 22° C. for 20 minutes. Following the incubations, the contents of the two tubes were combined over a period of 30 seconds, and incubated for an additional 20 minutes at 22° C. During this second incubation, the media in the seeded T-150 flask was removed and replaced with 14 ml Opti-MEM. The transfection mix was added to the flask and allowed to incubate at 37° C. for five hours. The transfection mix was then diluted with an equal volume of DMEM plus 20% FBS, 2% penicillin/streptomycin, and 2 mM hexamethylene bis-acetamide (HMBA), and incubated overnight at 34° C. The following day, media was removed and replaced with DMEM plus 10% FBS, 1% penicillin/streptomycin, and 2 mM HMBA. The packaging flask was incubated an additional three days before virus was harvested and stored at −80° C. until purification. Viral preparations were subsequently thawed, sonicated, clarified by centrifugation, and concentrated by ultracentrifugation through a 30% sucrose cushion. Viral pellets were resuspended in 100 µl PBS ($Ca^{2+}$ and $Mg^{2+}$ free) and stored at −80° C. for future use.

Virus Titering: Helper virus-containing stocks were titered for helper virus by standard plaque assay methods (Geschwind et al., *Brain Res. Mol. Brain Res.* 24:327-335, 1994). Amplicon titers for both helper virus-based and helper-free stocks were determined as follows. NIH 3T3 cells were plated in a 24-well plate at a density of $1\times10^5$ cells/well and infected with the virus. Twenty-four hours after viral infection, the monolayers were washed twice in PBS and either fixed with 4% paraformaldehyde and stained by X-gal histochemistry (HSVlac; 5 mM potassium ferricyanide; 5 mM potassium ferrocyanide; 0.02% NP-40; 0.01% sodium deoxycholic acid; 2 mM $MgCl_2$; and 1 mg/ml X-gal dissolved in PBS) or harvested for total DNA using lysis buffer (100 mM NaCl, 10 mM Tris, pH 8.0, 25 mM EDTA, 0.5% SDS) followed by phenol/chloroform extraction and ethanol precipitation. Real-time quantitative PCR was performed on duplicate samples using primers corresponding to the β-lactamase gene present in the amplicon plasmid, according to Bowers et al. (*Mol. Ther.* 1:294-299, 2000). Total DNA was quantitated and 50 ng of DNA was analyzed in a PE7700 quantitative PCR reaction using a designed β-lactamase-specific primer/probe combinatino multiplexed with an 18S rRNA-specific primer/probe set. The β-lactamase probe sequence was 5'-CAG-GACCACTTCTGCGCTCGGC-3' (SEQ ID NO:9); the β-lactamase sense primer sequence was 5'-CTGGATGGAG-GCGGATAAAGT-3' (SEQ ID NO:10); and the β-lactamaseantisense primer sequence was 5'-TGCTGGCACCA-GACTTGCCCTC-3' (SEQ ID NO: 11). The 18S rRNA probe sequence was 5'-TGCTGGCACCAGACTTGCCCTC-3' (SEQ ID NO:6); the 18S sense primer sequence was 5'-CG-GCTACCACATCCAAGGAA-3' (SEQ ID NO:7); and the 18S antisense primer sequence was 5'-GCTGGAATTAC-CGCGGCT-3' (SEQ ID NO:8). Helper virus titers (pfu/ml; plaque-forming units/ml), amplicon expression titers (bfu/ml; blue-forming units/ml), and amplicon transduction titers (TU/ml; transduction units/ml) obtained from these methods were used to calculate amplicon titer and thus standardize experimental viral delivery. Amplicon titers of the various virus preparations ranged from $4\text{-}5\times10^8$ bfu/ml while helper titers were in the range of $5\text{-}15\times10^7$ pfU/ml.

Mixed lymphocyte tumor reaction (MLTR) assay: CLL cells were transduced with equal transduction units of helper virus-containing or helper virus-free amplicon stocks, were irradiated (20 Gy), and were used as stimulators (2.5 or $5\times10^4$ cells/well) with allogeneic normal donor T cells ($2\times10^5$ cells in a final volume of 200 µl) in 96-well flat-bottom plates. All cultures were performed in triplicate. The cells were incubated 5 days at 37° C. in 5% $CO_2$. Cells were pulsed with 1 μCi ($^3$H)-thymidine for the last 18 hours of the culture period before being transferred onto a glass fiber filter and radioactive counts measured by liquid scintillation counting. To determine the involvement of Signal One, CLL cells were infected with equivalent transduction units of HSVlac, HSVB7.1, hf-HSVlac, or hf-HSVB7.1 and were used as stimulators as described above with or without phorbol 12-myristate 13-acetate (PMA) added to a final concentration of 10 ng/ml.

ELISA for IL-2 and γ-interferon: Culture supernatant (50 μl) from every well of the MLTR plate was collected on day 4 prior to adding ($^3$H)-thymidine and used in a standard sandwich ELISA (R&D Systems) according to manufacturer recommendations.

Cytotoxic T lymphocyte (CTL) Assay: T cells purified from normal donor peripheral blood mononuclear cells (PBMC) were incubated with uninfected irradiated CLL cells, helper virus-free HSVlac-, or helper virus-free HSVCD40L-infected CLL cells at a ratio of 4:1 and incubated for six days. A cytotoxicity assay was performed by incubating primed T cells with $1 \times 10^4$ $^{51}$Cr-labeled CLL cells in a V-shaped 96-well plate at varying effector:target ratios. Spontaneous release was measured by incubating $^{51}$Cr-labeled CLL cells alone while maximum release was calculated by lysing the cells with 2% Triton-X. After a six-hour incubation, supernatant was collected and radioactivity was measured using a γ-counter (Packard Instrument). Mean values were calculated for the triplicate wells and the results are expressed as % specific lysis according to the formula: experimental counts−spontaneous counts/total counts−spontaneous counts×100.

Results

HSV amplicon-mediated gene transfer into CLL cells. The utility of HSV-based amplicon vectors for transduction of CLL cells was examined according to the methods described above. HSV amplicon vectors encoding β-galactoside, CD80 (B7.1) or CD154 (CD40L) were packaged using either a standard helper virus (designated HSVlac, HSVB7.1 and HSVCD40L) or a helper virus-free method (designated hf-HSVlac, hf-HSVB7.1 and hf-HSVCD40L).

CLL cells were isolated by density gradient centrifugation and ≧97% of the cells stained for CD19, a cell surface marker for B lymphocytes. The cells were transduced with either HSVlac, HSVB7.1, hf-HSVlac, or hf-HSVB7.1. X-gal histochemistry was performed to detect the β-galactosidase (lacZ) transgene product expressed by HSVlac and hf-HSVlac, while fluorescence activated cell sorting (FACS) analyses were performed on CLL cells transduced with equivalent transduction units of HSVB7.1 and hf-HSVB7.1 (FIG. 10). More than 70% of the cells stained for either lacZ or B7.1 expression at an MOI of 1.0. In agreement with previous studies using HSVlac, expression levels of β-galactosidase peaked at 2-3 days and persisted for up to 7 days post-infection. Hence, both helper virus-containing and helper virus-free amplicon preparations appear to be effective for gene transfer into CLL cells.

Effect of helper virus on host cell MHC-I expression. Although both vector preparations were able to drive high-level expression of B7.1 in CLL cells, it was possible that helper virus-containing amplicon preparations disrupted MHC I-mediated antigen presentation. ICP-47, a gene present in the D30EBA helper virus, encodes a protein that blocks TAP-1 mediated peptide loading into MHC I. Expression of such an immunosuppressive activity would reduce the utility of HSV amplicon vectors for immunotherapeutic strategies. To examine this possibility, CLL cells were transduced with HSVB7.1 or hf-HSVB7.1 and examined by flow-cytometry for levels of B7.1 and MHC I expression.

Significant down-regulation of MHC I in CLL cells transduced with HSVB7.1 was observed compared to MHC I expression in uninfected cells (FIG. 11). In contrast, transduction with hf-HSB7.1 resulted in high levels of B7.1 expression and maintenance of MHC I surface expression on B7.1-transduced cells. These data highlight the role of HSV-encoded factors in modulation of host immunity and underscore a fundamental difference in the immunotherapeutic potential between helper virus-based and helper virus-free amplicon preparations.

Allogeneic T cell activation by HSV amplicon-transduced CLL cells. To assess functional differences in antigen presentation following transduction with helper virus-containing or helper virus-free amplicon stocks, the effects of B71. transduction on the ability of CLL cells to stimulate T cell proliferation in an allogeneic mixed leukocyte tumor reaction (MLTR) were analyzed. CLL cells were transduced with either HSVlac, HSVB7.1, hf-HSVlac, or hf-HSVB7.1 and transduced cells served as stimulators in an allogeneic MLTR using T cells from a normal donor. hf-HSVB7.1-transduced CLL cells were able to directly stimulate T cell proliferation. In spite of amplicon-directed expression of B7.1 on at least 70% of the CLL cells, HSVB7.1-transduced CLL cells failed to elicit a T cell proliferative response, suggesting that the antigen presenting capacity of the infected CLL cells had been seriously impaired. This could have occurred through the loss of MHC I expression or through some other mechanism mediated by the helper virus. Phorbol 12-myristate 13-acetate (PMA) was used to provide an extrinsic "signal one" to potentially compensate for the adverse effect elicited by the helper virus on CLL cells, thereby allowing transduced B7.1 to elicit a co-stimulatory signal to T cells. Provision of extrinsic Signal One by PMA resulted in significant proliferation in HSVB7.1-infected CLL cells (relative to non-transduced or HSVlac-transduced CLL cells). PM treatment also augmented proliferation in hf-HSVB7.1-transduced CLL cells, suggesting that the full potential of T cell activation by these transduced cells was not fully achieved by helper virus-free vector delivery alone.

Another correlate to T cell activation relates to induction of IL-2 secretion. Supernatants collected from the MLTR samples described above were analyzed using an IL-2 ELISA. IL-2 levels were highest when hf-HSVB7.1-transduced CLL cells were utilized as T cell stimulators (the uppermost Table in FIG. 11) as compared to HSVB7.1 or HSVlac-transduced cells. In other MLTR assays using HSVB7.1-transduced CLL cells, IL-2 secretion was dependent on provision of Signal One via PMA, as was observed with PMA-mediated rescue of T cell stimulators.

Up-regulation of co-stimulatory molecules on CLL cells transduced by HSV amplicons. Engagement of the CD40 receptor on APCs is a critical step in the initiation of an immune response. Up-regulation of costimulatory molecules on CLL cells induced by CD40 receptor signaling correlates with a cell's ability to function as an APC (van Kooten et al., *Curr. Opin. Immunol.* 9:330-337, 1997; Gruss et al., *Leuk. Lymphoma* 24:393-422, 1997). We selected endogenous B7.1 expression as a surrogate marker for the morphologic changes induced by CD40 receptor engagement in CLL cells. To test for paracrine and autocrine induction of B7.1, CLL cells were transduced with either hf-HSVCD40L or hf-HSVlac, incubated for six days and subsequently analyzed for expression of endogenous B7.1. Transduction with hf-HSVCD40L resulted in up-regulation of B7.1 on CLL cells as compared to untransduced and hf-HSVlac transduced cells.

The percentage of CLL cells expressing B7.1, CD40L, or both, was quantitated by two-color flow cytometry (the middle Table in FIG. 11). Although infection of CLL cells with HSVCD40L resulted in more than 70% of the cells expressing CD40L, the percentage of cells expressing endogenous B7.1 did not increase over background levels observed in cells transduced with control vector. CLL cells infected with hf-HSVCD40L exhibited a marked enhancement of B7.1 expression. The discrepancy at the level of endogenous B7.1 expression between CLL cells transduced with HSVCD40L and hf-HSVCD40L cannot be attributed to different efficiencies of infectivity as both grouped expressed similar levels of CD40L. Similar experiments using CD19 expression as an endogenous cell marker confirmed an inverse relationship between surface CD19 expression and CD40L expression in cells transduced with helper virus-containing HSVCD40L, but not in cells transduced with hf-HSVCD40L. These data suggested that transduction with HSVCD40L resulted in a decrease in expression level of endogenous B7.1

Subsequently, the ability of CLL cells transduced by CD40L to serve as stimulators in an allogeneic MLTR was examined. CLL cells were transduced with hf-HSVlac, hf-HSVCD40L, HSVlac, or HSVCD40L and incubated for 4-6 days to allow for up-regulation of co-stimulatory molecules and then used as stimulators in an allogeneic MLTR. Although similar levels of CD40L expression were observed following transduction with either HSVCD40L or hf-HSVCD40L, cells transduced with hf-HSVCD40L were more potent T cell stimulators than those transduced with HSVCD40L or control vectors.

hf-HSV amplicon transduced CLL stimulate allogeneic CTL. Since the goal of immune therapy is to generate tumor-specific CTL, and in view of the data above showing superiority of helper virus-free stock, we tested the capacity of allogeneic T cells to elicit a cytotoxic response against CLL cells transduced with hf-HSVCD40L. T cells purified from normal donor peripheral blood mononuclear cells (PBMC) were incubated for six days with non-transduced/irradiated CLL cells, hf-HSVlac-, or hf-HSVCD40L-transduced CLL cells. A cytotoxicity assay was performed by incubating primed T cells with $^{51}$Cr-labeled CLL cells at varying effector to target ratios. Significantly higher CTL activity was generated by priming with hf-HSVCD40L-transduced CLL cells compared to control or hf-HSVlac-transduced cells. As another index of cytolytic T cell activation, we measured levels of gamma-interferon secretion. High levels of IFN-gamma were secreted by hf-HSVCD40L-transduced CLL stimulated T cells as detected by ELISA (the lower Table in FIG. 11), suggesting that helper virus-free amplicon stocks can effectively transduce CLL cells to serve as tumor vaccines.

DCs pulsed with CTL peptide epitopes derived from tumor antigens or transduced with adenoviral vectors that direct expression of tumor antigens have been shown to elicit anti-tumor CTL activity. However, each of these methods has limitations. For example, to use peptides for tumor immunotherapy, one would have to recognize CTL epitopes for tumor antigens in multiple HLA types and, with adenoviral vectors, the viral gene products expressed in transduced cells can lead to anti-vector immunity, which would preclude multiple immunizations.

Example 12

LIGHT, a TNF Family Member Enhances the Antigen Presenting Capacity of Chronic Lymphocytic Leukemia and Stimulates Autologous Cytolytic T Cells CLL B cells possess the ability to process and present tumor antigens, but lack expression of costimulatory molecules, rendering them inefficient effectors of T-cell activation. We previously demonstrated that helper virus-free preparations of Herpes Simplex Virus (HSV) amplicon vectors encoding CD40L efficiently transduce CLL B cells and render them capable of eliciting specific anti-tumor T-cell responses (Tolba et al., *Blood* 98:287-295, 2001). LIGHT (TNFSF14), a member of the TNF superfamily, represents a strong candidate molecule as it efficiently activates T cells as well as antigen-presenting cells (APC). We employed an HSV amplicon vector expressing human LIGHT (hf-HSV-LIGHT) to transduce CLL B cells and compared the immunomodulatory function and T-cell activation by hf-HSV-LIGHT to that of the previously described CD40L-expressing amplicon (hf-HSVCD40L). hf-HSVLIGHT transduction induced expression of endogenous B7.1, B7.2 and ICAM. 1, albeit to a lesser degree than observed in response to CLL B cells transduced with hf-HSV-CD40L. hf-HSVLIGHT enhanced antigen-presenting capacity of CLL B cells and stimulated T cell proliferation in an allogeneic mixed lymphocyte tumor reaction (MLTR) through a dual mechanism: a) indirectly through induction of native B7.1/B7.2 and b) directly via stimulation of Hve-A receptor on T cells. Finally, hf-HSVLIGHT transduced CLL B cells successfully stimulated outgrowth of autologous cytotoxic T-lymphocytes in vitro. These data suggest that hf-HSVLIGHT transduction may be useful for induction of immune responses to CLL and other B-cell lymphoid malignancies.

What is claimed is:

1. A method of treating a patient who has cancer, or who may develop cancer, the method comprising
   (a) transducing dendritic cells of the patient ex vivo with an HSV amplicon particle, wherein the particle is made by a helper virus-free method comprising: (i) providing a virus packaging cell that has been stably transfected with a nucleic acid sequence that encodes an accessory protein; and (ii) transfecting the virus packaging cell with one or more packaging vectors that, individually or collectively, encode one or more HSV structural proteins but do not encode a functional herpes virus cleavage/packaging site and an amplicon plasmid comprising a functional herpes virus cleavage/packaging site, a herpes virus origin of DNA replication, and a sequence encoding an immunostimulatory protein under the control of a promoter, thereby producing transduced dendritic cells; and
   (b) administering the transduced dendritic cells to the patient, wherein the transduced dendritic cells express a tumor specific antigen.

2. The method of claim 1, wherein the accessory protein is a virion host shutoff (vhs) protein.

3. The method of claim 2, wherein the vhs protein is an HSV-1 vhs protein, an HSV-2 vhs protein, an HSV-3 vhs protein, a bovine herpes virus 1 vhs protein, a bovine herpes virus 1.1 vhs protein, a gallid herpes virus 1 vhs protein, a gallid herpes virus 2 vhs protein, a suid herpes virus 1 vhs protein, a baboon herpes virus 2 vhs protein, a pseudorabies virus vhs protein, a cercopithecine herpes virus 7 vhs protein, a meleagrid herpes virus 1 vhs protein, an equine herpes virus 1 vhs protein, or an equine herpes virus 4 vhs protein.

4. The method of claim 2, wherein the vhs protein is operatively coupled to its native transcriptional control elements.

5. The method of claim 1, wherein the accessory protein is a VP16 protein.

6. The method of claim 5, wherein the VP16 protein is an HSV1 VP16, an HSV-2 VP16, a bovine herpes virus 1 VP16, a bovine herpes virus 1.1 VP16, a gallid herpes virus 1 VP16, a gallid herpes virus 2 VP16, a meleagrid herpes virus 1 VP16, or an equine herpes virus 4 VP16.

7. The method of claim 1, wherein the one or more packaging vectors comprises a cosmid, a yeast artificial chromosome, a bacterial artificial chromosome, a human artificial chromosome, or an F element plasmid.

8. The method of claim 7, wherein the one or more packaging vectors comprises a set of cosmids comprising cos6Δa, cos28, cos14, cos56, and cos48Δa.

9. The method of claim 1, wherein the immunostimulatory protein is a cytokine, a costimulatory molecule, or a tumor-specific antigen.

10. The method of claim 9, wherein the cytokine is an interleukin, an interferon, or a chemokine.

11. The method of claim 9, wherein the costimulatory molecule is a B7 molecule or CD40L.

12. The method of claim 1, wherein the cancer is a hematologic malignancy, a lymphoma, a melanoma, a glioblastoma, a pancreatic cancer, a cancer of the reproductive system, a cancer of the endocrine system, a neuroblastoma, breast cancer, colorectal cancer, stomach cancer, cancer of the throat or mouth, lung cancer, or bladder cancer.

13. A method of treating a patient who has cancer, or who may develop cancer, the method comprising
   (a) transducing dendritic cells of the patient ex vivo with an HSV amplicon particle, wherein the particle is made by a helper virus-free method comprising providing a virus packaging cell and transfecting the cell with (i) one or more packaging vectors that, individually or collectively, encode one or more HSV structural proteins but do not encode a functional herpes virus cleavage/packaging site, (ii) an amplicon plasmid comprising sequences that encode a functional herpes virus cleavage/packaging site, a herpes virus origin of DNA replication, and a sequence that encodes an immunostimulatory protein under the control of a promoter, and (iii) a nucleic acid sequence that encodes an accessory protein, thereby producing transduced dendritic cells; and
   (b) administering the transduced dendritic cells to the patient, wherein the transduced dendritic cells express a tumor specific antigen.

14. The method of claim 13, wherein the accessory protein is a virion host shutoff (vhs) protein.

15. The method of claim 14, wherein the vhs protein is an HSV-1 vhs protein, an HSV-2 vhs protein, an HSV-3 vhs protein, a bovine herpes virus 1 vhs protein, a bovine herpes virus 1.1 vhs protein, a gallid herpes virus 1 vhs protein, a gallid herpes virus 2 vhs protein, a suid herpes virus 1 vhs protein, a baboon herpes virus 2 vhs protein, a pseudorabies virus vhs protein, a cercopithecine herpes virus 7 vhs protein, a meleagrid herpes virus 1 vhs protein, an equine herpes virus 1 vhs protein, or an equine herpes virus 4 vhs protein.

16. The method of claim 14, wherein the vhs protein is operatively coupled to its native transcriptional control elements.

17. The method of claim 13, wherein the accessory protein is a VP16 protein.

18. The method of claim 17, wherein the VP16 protein is an HSV1 VP16, an HSV-2 VP16, a bovine herpes virus 1 VP16, a bovine herpes virus 1.1 VP16, a gallid herpes virus 1 VP16, a gallid herpes virus 2 VP16, a meleagrid herpes virus 1 VP16, or an equine herpes virus 4 VP16.

19. The method of claim 13, wherein the one or more packaging vectors comprises a cosmid, a yeast artificial chromosome, a bacterial artificial chromosome, a human artificial chromosome, or an F element plasmid.

20. The method of claim 19, wherein the one or more packaging vectors comprises a set of cosmids comprising cos6Δa, cos28, cos14, cos56, and cos48Δa.

21. The method of claim 13, wherein the immunostimulatory protein is a cytokine, a costimulatory molecule, or a tumor-specific antigen.

22. The method of claim 21, wherein the cytokine is an interleukin, an interferon, or a chemokine.

23. The method of claim 21, wherein the costimulatory molecule is a B7 molecule or CD40L.

24. The method of claim 13, wherein the cancer is a hematologic malignancy, a lymphoma, a melanoma, a glioblastoma, a pancreatic cancer, a cancer of the reproductive system, a cancer of the endocrine system, a neuroblastoma, breast cancer, colorectal cancer, stomach cancer, cancer of the throat or mouth, lung cancer, or bladder cancer.

25. A method of treating a patient who has cancer, or who may develop cancer, the method comprising
    (a) transducing tumor cells of the patient ex vivo with an HSV amplicon particle, wherein the particle is made by a helper virus-free method comprising: (i) providing a virus packaging cell that has been stably transfected with a nucleic acid sequence that encodes an accessory protein; and (ii) transfecting the virus packaging cell with one or more packaging vectors that, individually or collectively, encode one or more HSV structural proteins but do not encode a functional herpes virus cleavage/packaging site and an amplicon plasmid comprising a functional herpes virus cleavage/packaging site, a herpes virus origin of DNA replication, and a sequence encoding an immunostimulatory protein under the control of a promoter, thereby producing transduced tumor cells; and
    (b) administering the transduced tumor cells to the patient.

26. The method of claim 25, wherein the accessory protein is a virion host shutoff (vhs) protein.

27. The method of claim 26, wherein the vhs protein is an HSV-1 vhs protein, an HSV-2 vhs protein, an HSV-3 vhs protein, a bovine herpes virus 1 vhs protein, a bovine herpes virus 1.1 vhs protein, a gallid herpes virus 1 vhs protein, a gallid herpes virus 2 vhs protein, a suid herpes virus 1 vhs protein, a baboon herpes virus 2 vhs protein, a pseudorabies virus vhs protein, a cercopithecine herpes virus 7 vhs protein, a meleagrid herpes virus 1 vhs protein, an equine herpes virus 1 vhs protein, or an equine herpes virus 4 vhs protein.

28. The method of claim 27, wherein the vhs protein is operatively coupled to its native transcriptional control elements.

29. The method of claim 25, wherein the accessory protein is a VP16 protein.

30. The method of claim 29, wherein the VP16 protein is an HSV1 VP16, an HSV-2 VP16, a bovine herpes virus 1 VP16, a bovine herpes virus 1.1 VP16, a gallid herpes virus 1 VP16, a gallid herpes virus 2 VP16, a meleagrid herpes virus 1 VP16, or an equine herpes virus 4 VP16.

31. The method of claim 25, wherein the one or more packaging vectors comprises a cosmid, a yeast artificial chromosome, a bacterial artificial chromosome, a human artificial chromosome, or an F element plasmid.

32. The method of claim 25, wherein the one or more packaging vectors comprises a set of cosmids comprising cos6Δa, cos28, cos14, cos56, and cos48Δa.

33. The method of claim 25, wherein the immunostimulatory protein is a cytokine or a costimulatory molecule.

34. The method of claim 33, wherein the cytokine is an interleukin, an interferon, or a chemokine.

35. The method of claim 33, wherein the costimulatory molecule is a B7 molecule or CD40L.

36. The method of claim 25, wherein the cancer is a hematologic malignancy, a lymphoma, a melanoma, a glioblastoma, a pancreatic cancer, a cancer of the reproductive system, a cancer of the endocrine system, a neuroblastoma, breast cancer, colorectal cancer, stomach cancer, cancer of the throat or mouth, lung cancer, or bladder cancer.

37. A method of treating a patient who has cancer, or who may develop cancer, the method comprising
    (a) transducing tumor cells of the patient ex vivo with an HSV amplicon particle, wherein the particle is made by a helper virus-free method comprising providing a virus packaging cell and transfecting the cell with (i) one or more packaging vectors that, individually or collectively, encode one or more HSV structural proteins but do not encode a functional herpes virus cleavage/packaging site, (ii) an amplicon plasmid comprising sequences that encode a functional herpes virus cleavage/packaging site, a herpes virus origin of DNA replication, and a sequence that encodes an immunostimulatory protein under the control of a promoter, and (iii) a nucleic acid sequence that encodes an accessory protein, thereby producing transduced tumor cells; and
    (b) administering the transduced tumor cells to the patient.

38. The method of claim 37, wherein the accessory protein is a virion host shutoff (vhs) protein.

39. The method of claim 38, wherein the vhs protein is an HSV-1 vhs protein, an HSV-2 vhs protein, an HSV-3 vhs protein, a bovine herpes virus 1 vhs protein, a bovine herpes virus 1.1 vhs protein, a gallid herpes virus 1 vhs protein, a gallid herpes virus 2 vhs protein, a suid herpes virus 1 vhs protein, a baboon herpes virus 2 vhs protein, a pseudorabies virus vhs protein, a cercopithecine herpes virus 7 vhs protein, a meleagrid herpes virus 1 vhs protein, an equine herpes virus 1 vhs protein, or an equine herpes virus 4 vhs protein.

40. The method of claim 38, wherein the vhs protein is operatively coupled to its native transcriptional control elements.

41. The method of claim 37, wherein the accessory protein is a VP16 protein.

42. The method of claim 41, wherein the VP16 protein is an HSV1 VP16, an HSV-2 VP16, a bovine herpes virus 1 VP16, a bovine herpes virus 1.1 VP16, a gallid herpes virus 1 VP16, a gallid herpes virus 2 VP16, a meleagrid herpes virus 1 VP16, or an equine herpes virus 4 VP16.

43. The method of claim 37, wherein the one or more packaging vectors comprises a cosmid, a yeast artificial chromosome, a bacterial artificial chromosome, a human artificial chromosome, or an F element plasmid.

44. The method of claim 37, wherein the one or more packaging vectors comprises a set of cosmids comprising cos6Δa, cos28, cos14, cos56, and cos48Δa.

45. The method of claim 37, wherein the immunostimulatory protein is a cytokine or a costimulatory molecule.

46. The method of claim 45, wherein the cytokine is an interleukin, an interferon, or a chemokine.

47. The method of claim 45, wherein the costimulatory molecule is a B7 molecule or CD40L.

48. The method of claim 37, wherein the cancer is a hematologic malignancy, a lymphoma, a melanoma, a glioblastoma, a pancreatic cancer, a cancer of the reproductive system, a cancer of the endocrine system, a neuroblastoma, breast cancer, colorectal cancer, stomach cancer, cancer of the throat or mouth, lung cancer, or bladder cancer.

* * * * *